US008071545B2

(12) United States Patent  
Coleman

(10) Patent No.: US 8,071,545 B2
(45) Date of Patent: Dec. 6, 2011

(54) THERAPIES AND COMPOSITIONS FOR CONTROLLING THE STRESS MECHANISM AND FOR STABILIZING HEMOSTASIS IN AN ORGANISM

(75) Inventor: Lewis S. Coleman, Bakersfield, CA (US)

(73) Assignee: Lewis S. Coleman, MD, Inc., Bakersfield, CA (US)

( * ) Notice: Subject to any disclaimer, the term of this patent is extended or adjusted under 35 U.S.C. 154(b) by 1305 days.

(21) Appl. No.: 11/080,709

(22) Filed: Mar. 15, 2005

(65) Prior Publication Data

US 2006/0211611 A1 Sep. 21, 2006

(51) Int. Cl.
*A61K 31/36* (2006.01)
(52) U.S. Cl. ............... 514/12; 514/2; 435/7.1
(58) Field of Classification Search ............. None
See application file for complete search history.

(56) References Cited

U.S. PATENT DOCUMENTS 6,284,260 B1 * 9/2001 Czeizler ............ 424/423

OTHER PUBLICATIONS

Giraldi et al. (Annals of the New York Academy of Sciences, vol. 917, pp. 549-559, 2000).*
Hong Im et al. (Cancer Research, vol. 64, pp. 8613-8619, Dec. 1, 2004).*
Thornton et al. (Circulation, vol. 69, pp. 721-727, 1984).*
von Kanel et al. (Thromb. Haemost., vol. 92, pp. 1327-1335, 2004).*
Levine et at. (Psychosomatic Medicine, vol. 16, No. 5, 1954).*
Kehlet et al. (The Lancet, vol. 362, Dec. 6, 2003).*
Zacharski (Cancer Letters, vol. 186, pp. 1-9, 2002).*

* cited by examiner

*Primary Examiner* — Hope Robinson
(74) *Attorney, Agent, or Firm* — Cislo & Thomas, LLP

(57) ABSTRACT

A method for treating skin malignancies, malignant tumors, metastatic malignancies and abnormal skin growths in an organism by treating the organism to inhibit the stress mechanism via different pathways and synergistically reduce the production of thrombin in the organism by maintaining antinociception anesthesia throughout the treatment process to control psychic and somatic stress and to reduce the activity levels of Factor VIII, administering medications to the organism that reduce the activity of Factor VII, administering antithrombin medications to the organism, or administering to the organism medications that reduce the activity levels of Factor X and Factor Xa.

22 Claims, 3 Drawing Sheets

THERAPIES AND COMPOSITIONS FOR CONTROLLING THE STRESS MECHANISM AND FOR STABILIZING HEMOSTASIS IN AN ORGANISM

FIELD OF THE INVENTION

This invention relates to methods useful in treating surgical stress syndrome, circulatory disorders, malignancies and for providing a blood substitute in an organism. The methods and treatments disclosed herein include methods and compositions that stabilize the turbulence of an organism's blood in order to treat stress-related disease.

BACKGROUND OF INVENTION

A Unified Theory of Stress, Coagulation, Inflammation, Wound Healing, Embryological Development and Tissue Maintenance Stress, n.: 1. —The reaction of the animal body to forces of a deleterious nature, infections and various abnormal states that tend to disturb its normal physiologic equilibrium (homeostasis). 2. —The resisting force set up in a body as a result of an externally applied force.(1)

Disorder is the basic law of the universe. Living creatures are ordered forms that employ combinations of information systems, chemical reactions, and mechanical mechanisms to acquire energy from their environment to maintain their structural integrity and function, and replicate. To be alive is to be unceasingly stressed by the demands of energy acquisition and structural maintenance.

Occam's Razor, a key concept in scientific philosophy, suggests that the best approach to a complex problem is to assume that the simplest explanation, or set of explanations, is correct until proven otherwise.

It has long been understood that humans and animals are equipped with physiological mechanisms that enable them to resist and repair the damaging effects of stressful stimulus, including coagulation, inflammation, scab formation, wound repair, and tissue maintenance. The observed reactions to stress are numerous, confusing and inter-related(2,3), and thus far no attempt has been made to describe a single mechanism that can explain these various phenomena. This manuscript will present a theory ("Stress Theory") that endeavors to explain the biological reaction to stressful stimuli in terms of a simple, unified physiologic mechanism. The formulation of the theory was inspired by the author's observations of the clinical benefits of opioid-based anesthetic strategies, and has been greatly facilitated by recently published studies. It is intended to inspire new research that may lead to improved surgical outcome as well as general advance of medical understanding.

The Stress Theory may provide fresh insights to the nature of embryology, neonatology(4), physiology, immunology, pharmacology, and pathology. It may offer improved understanding of the mechanisms of drug actions, systemic vascular resistance, blood flow and distribution, blood pressure, atherosclerosis, thromboembolism, capillary homeostasis, apoptosis, embryological tissue development, muscle hypertrophy, athletic cardiovascular "conditioning", blood coagulation, tissue inflammation, wound healing, Virchow's Triad, the "Fight or Flight" stress syndrome of Hans Seyle, Surgical stress, tissue remodeling and maintenance and numerous manifestations of pathology by describing all these in terms of the effects of a cohesive stress-opposing mechanism that operates continuously to maintain homeostasis and tissue integrity in the animal body(5).

Presently accepted coagulation "Cascade" theory provides an incomplete description of the coagulation process that defines coagulation Factors VII and VIII and thrombin as enzymatic proteins that react with one another and other blood-borne proteins to effect clot formation. Stress Theory is predicated on the alternate hypothesis that coagulation factors VII and VIII are blood-borne stress agents that respectively cause local and systemic elevations of thrombin levels and synergize each other's actions to produce hyper-elevations of thrombin at the site of stress (injury), and that thrombin is responsible for the numerous symptoms and effects exerted by the stress mechanism. Stress Theory offers a simpler and more complete explanation of hemostasis and coagulation than presently prevailing Cascade Theory, plus a simple explanation of wound healing, tissue maintenance, and important aspects of embryological development that is presently lacking.

Stress Theory assigns a role to Factor VII that might be compared to the "Extrinsic" cascade. It circulates in flowing blood and is separated from exposure to the underlying collagen that constitutes the major component of blood vessel structure by the vascular endothelium, which is only one cell layer in thickness. Disruption of the vascular endothelium therefore exposes factor VII to collagen, causing its activation. Its activity is normally localized and it focuses the effects of the Stress Mechanism at the site of injury (stress).

Likewise, the role of Factor VIII loosely corresponds to the "Intrinsic" cascade. It is a hormone that is produced and released directly into the blood by the vascular endothelium, a gland, under the control of the Sympathetic Nervous System (SNS), so that its blood level varies in accord with the tone and activity levels of the SNS. Its activity is systemic and its function is to regulate the activity level of the Stress Mechanism.

Both Factors VII and Factor VIII activate thrombin, and their combined effects cause localized hyper-elevations of thrombin that focus the effects of the stress mechanism at the site of stress and injury. The role of thrombin thus corresponds to the "Final Common Pathway" as described by Cascade Theory.

Stress Theory hypothesizes that thrombin is the primary enzymatic effecter agent of the stress mechanism. Thrombin is the known cause of numerous effects, including platelet activation(6), cell mitosis(7), cell hypertrophy, increased cell metabolism, inflammation(2), collagen production, and the conversion of fibrinogen to insoluble fibrin(8). It is closely associated with embryological development, wound healing, coagulation, malignancy, and tissue maintenance. Stress Theory hypothesizes Is that thrombin produces these multiple effects by means of a common mechanism that has yet to be identified.

Stress Theory postulates two mechanisms of hemostasis, both of which are controlled by blood levels of thrombin and "insoluble" fibrin. These are: 1. Capillary Hemostasis, which is initiated by closure of a molecular level Capillary Gate Mechanism governed by varying levels of "insoluble" fibrin and 2. Systemic Hemostasis, which is manifested by the familiar blood clot formation process that occurs in larger vessels. This is initiated by declines in blood turbulence and mixing that are initiated by increased blood levels of "insoluble" fibrin, a three-dimensional molecule with physical properties absent in its precursor, "soft" fibrin, and further enhanced by the formation of fibrin strands that connect various blood components to one another as turbulence and mixing decline.

The theory implies that changes in systemic vascular resistance occur in accord with the operation of the Capillary Gate mechanism and the degree of capillary hemostasis(9) as opposed to muscular contraction or relaxation of larger blood vessels. It asserts that the rapidly reversible physical properties of the three-dimensional matrix structure of insoluble fibrin, as controlled and facilitated by varying levels of Factor VIII, enable it to open and close the hypothesized Capillary Gate Mechanism to produce capillary hemostasis and indirectly regulate capillary perfusion. Simultaneously, insoluble fibrin increases systemic blood viscosity, which reduces blood turbulence and mixing, thereby increasing blood coagulability and thereby inducing clot formation. Hyper-elevations of insoluble fibrin in the immediate vicinity of stressful stimulus (injury), determined by the combined effects of Factors VII and VIII, reduce turbulence and mixing below a critical threshold, whereupon fibrin strands form inter-connections among blood components that further reduce turbulence and mixing, and clot formation proceeds to completion.

Chronic systemic elevations in blood viscosity, caused by persistent stressful stimulus and other factors cause reductions in blood turbulence and mixing that accelerate atherosclerosis in the arterial tree and increase the risk of thromboembolism in the venous system(10). Systemic vascular resistance and blood pressure(11) vary directly, and cardiac output and tissue perfusion vary inversely(12), with the degree of closure of the Capillary Gate mechanism as determined by the level of stress, SNS activation, and Factor VIII release.

Although thrombin plays an essential role in coagulation, most thrombin generation occurs after clot formation, suggesting that it may have additional functions(13,14). Stress Theory postulates that thrombin initiates coagulation and inflammation as a prelude to wound healing, and attracts various wound-healing cell types to the site of injury(15,16). It subsequently induces fibroblast mitosis, metabolism, proliferation and collagen production(17) as an integral part of the wound healing process. Thrombin levels continue to be elevated at the site of stress to regulate the wound-healing process in accord with continued collagen exposure to flowing blood, which maintains Factor VII activation. When wound healing is substantially complete, and collagen is sealed from exposure to flowing blood, thrombin levels fall. The decline in thrombin levels induces fibroblast apoptosis, signaling an end to the "active phase" of wound healing(18, 19).

Maintenance levels of thrombin may stimulate collagen replenishment and tissue maintenance and remodeling, as evidenced by skin necrosis and ulceration and disturbances of wound repair(20) that sometimes result from treatment with coumadin, which exerts anti-thrombin effects(21-23).

Growing evidence suggests that the embryological development of complex multi-celled eukaryotic organisms may be largely governed by genetic programming contained in "junk" DNA in the form of "introns" that in the case of humans constitutes 95 percent or more of the genome(24). The introns may exert their effects on embryological development by controlling the timing of developmental processes, such as stem cell maintenance, cell proliferation, and apoptosis(25). Thrombin has been shown to be closely associated with cell maintenance(26), metabolism(27), hypertrophy(28-30), proliferation(31), angiogenesis(32) and apoptosis(19), and thrombin appears to play an important role in embryological development, as evidenced by fetal developmental defects that are associated with the administration of thrombin inhibitors to pregnant females and studies that demonstrate the role of thrombin in embryological development (31,33,34). I therefore hypothesize that introns control embryological development by controlling localized thrombin levels at precise time intervals. The stress mechanism, which also governs thrombin levels, may play a complimentary and synergistic role in embryological development by stimulating newly-developed organs and tissues to grow and enlarge in response to the stresses associated with fetal development. Assuming the presence of thrombin-sensitive growth and mitosis receptors common to all cells, the combined effects of introns and the stress mechanism to regulate thrombin levels may provide a simplified explanation of embryological development in complex organisms.

Nearly all forms of disease cause activation of the stress mechanism, typically manifested by a triad of 1. elevated blood levels of Factor VIII, 2. increased blood viscosity and 3. increased blood coagulability. These are often accompanied by a wide variety of seemingly unrelated pathological symptoms(35) due to inflammation, fibrin generation, and fibroblast proliferation. The stress mechanism may account for these symptoms. The Stress Mechanism is powerful, and may cause pathological effects, including malignancy, that are at odds with its healing function. Understanding the cause of these symptoms may offer insight into the nature of several hitherto mysterious stress-related diseases, such as rheumatoid disease(36), the tissue damage of diabetes, ARDS, asthma, inflammatory bowel disease(37-39), malignancy, eclampsia(40) and DIC. It may explain how stress-related conditions appear to exaggerate the incidence and severity of one another, as in diabetes and pregnancy, or in CREST syndrome(41). It may explain the fact that patients afflicted with one form of cancer are at increased risk of additional forms of cancer, how conditions that activate the stress mechanism may increase the risk of atherosclerosis and malignancy(42) and how environmental factors may increase the risk of stress-related disease(43,44). It may explain the associations between hypertension, systemic vascular resistance, blood viscosity(5), blood coagulability, atherosclerosis, and heart disease(45,46). It may suggest new forms of treatment and research. Finally, it may offer a logical way to employ anesthesia and surgical techniques to control stress and improve surgical outcome.

DESCRIPTION OF THE RELATED ART

The Basics of Stress Theory

The Stress Theory is based on a set of inter-related, testable hypotheses. These are:

1. A Stress Mechanism is present in all vertebrate species that involves the activities of Factors VII and VIII and thrombin and operates continuously to control coagulation, scab formation, wound healing and tissue maintenance. "Stress" is any stimulus that causes activation of the Stress Mechanism.

2. There exists a sub-microscopic, molecular-level Capillary Gate Mechanism that is controlled by the effects of Factors VII and VIII and is an integral component of the Stress Mechanism. The Capillary Gate Mechanism regulates capillary hemostasis. The degree of capillary hemostasis (closure of the Capillary Gate Mechanism) indirectly affects capillary bed perfusion, systemic vascular resistance, blood pressure, and cardiac output.

3. Factor VIII is a systemic stress hormone that is continuously released into the bloodstream by a gland, the vascular endothelium, under the direct control of the Sympathetic Nervous System (SNS) in accord with constantly varying levels of stressful stimulus. Its function is to control the activity level of the Stress Mechanism. It consists of VIIIC and Von Willebrand's (VWF) components. Its VIIIC component causes the systemic conversion of prothrombin to thrombin and the activation of Factor XIII, which adds fibronectin cross-links to developing fibrin strands to form a three-dimensional "insoluble" fibrin molecule. The VWF component stabilizes, enhances and prolongs the function of the VIIIC component, thereby indirectly affecting thrombin activity. The VWF molecule also serves as a molecular component of the Capillary Gate.

4. Factor VII is a companion stress agent that is activated by exposure to collagen(47). Its actions occur at the site of tissue disruption(48,49). Like Factor VIII, it catalyzes the conversion of prothrombin to thrombin and thereby synergizes with the effects of Factor VIII to produce localized hyper-elevations of thrombin and focus the effects of the stress mechanism on the site of stress (injury).

5. Elevated blood levels of thrombin cause elevated blood levels of insoluble fibrin. Insoluble fibrin simultaneously causes both closure of the Capillary Gate Mechanism and elevations in blood viscosity. Increased blood viscosity causes "damping" (decrease) in blood turbulence and mixing(26). Thrombin also stimulates the activation of fibroblasts and other cell types to control embryonic organ development, wound healing and tissue maintenance.

6. Turbulence and mixing induced by pulsatile blood flow inhibits both atherosclerosis and coagulation(50). Coagulation occurs spontaneously when turbulence and mixing fall below a critical threshold. Atherosclerosis is accelerated by chronically lowered levels of turbulence and mixing in the blood.

7. Under ordinary circumstances, coagulation occurs only in the presence of the combined effects of Factors VII and VIII. Their effects synergize so as to induce hyper-elevations of thrombin at the site of injury that lowers turbulence and mixing below the threshold of clot formation.

8. The VIIIC component of Factor VIII is so unstable as to be completely inactive in the absence of VWF. Variations in the quality and/or quantity of VWF therefore cause variations in both the half-life and activity levels of Factor VIII. This explains the various coagulation-enhancing effects of VWF. It also explains how increased levels of stress cause the half-life of Factor VIII to be prolonged regardless of subsequent lowering of SNS activity levels.

9. The other effects of thrombin, including inflammation, cell proliferation, collagen production and increased cell metabolism are regulated by the Stress Mechanism in the same manner as coagulation so as to govern the wound-healing process, key aspects of embryological development, and tissue remodeling and maintenance.

10. Factor VIII is released in response to pure psychic stress (51) and thereby causes pre-emptive elevations in blood coagulability and capillary hemostasis so as to minimize blood loss in the event of subsequent injury. It functions as an integral part of the "fight or flight" stress phenomenon described by Hans Selye.

11. The hitherto mysterious pathological effects associated with Surgical Stress and the Stress Syndrome, including dementia, stroke, myocardial infarction(52), bowel ileus, vasomotor instability and sudden death are primarily explained by widespread and prolonged stress-induced closure of the Capillary Gate Mechanism that results in tissue oxygen starvation and damage in affected capillary beds.(53) This will be called "Capillary Fibrin Stress" (CFS). Microvascular disturbances in nervous tissue may offer an example of CFS(54-57).

12. Apoptosis is caused by a sudden decline of thrombin levels below a critical threshold required to sustain fibroblast metabolism and mitosis.(18) This normally signifies the completion of the active phase of wound healing and plays a critical role in embryological development.

13. Malignancy is an aberration of the wound-healing process in which prolonged and excessive levels of stressful stimulus and hyper-elevated thrombin levels cause the invasion of normal tissues by thrombin-activated fibroblasts, resulting in a self-sustaining release of thrombin that inhibits apoptosis.

14. SNS activity levels are stimulated by semi-independent pathways for psychic stress (conscious awareness of pain and danger) and somatic stress (physical tissue disruption). The simultaneous control of both psychic and somatic stress is necessary to produce synergistic reductions in SNS and Stress Mechanism activity levels that may prevent CFS, systemic inflammation, hypercoagulability and other pathological effects of stressful stimuli and Surgical Stress.

The various elements of the Stress Theory will be discussed in detail. Clinical examples, including eclampsia, essential hypertension, diabetes, DIC, and ARDS will be offered as illustrations of the role that stress may play in disease.

FIG. 1 shows a diagram providing an outline of the proposed Stress Mechanism.

Capillary Gate Mechanism

Recent advances in the understanding of the characteristics of Factor VIII may offer fresh insight as to the presence and nature of a fast-acting, sub-microscopic, molecular-level Capillary Gate Mechanism. A mechanism that regulates blood flow and hemostasis at the capillary level has long been suspected, but never identified(58-60). The Capillary Gate hypothesis is attractive for several reasons. It offers an explanation of observed capillary hemostasis, where none presently exists. Capillaries lack musculature, and cannot contract, so capillary vasoconstriction is impossible. However, capillaries and vascular endothelium have been shown to be innervated with both sympathetic and parasympathetic nerve endings(61) that may govern the release of Factor VIII and other vasoactive substances. Theories of capillary endothelial cell swelling that occlude the capillary lumen have been proposed, but are not supported by evidence. Theories of pre-capillary sphincter contraction that might explain capillary hemostasis are likewise lacking in substance, because pre-capillary sphincters and vessels invariably relax after short periods of contraction, and then exhibit compensatory vasodilation.

The Capillary Gate hypothesis also offers an improved explanation for the regulation of blood flow and distribution and systemic vascular resistance(62). The surface area of the capillaries is many times greater than that of all larger vessels combined, and the hemodynamic pressures and flows are vastly lower, so that control of blood flow might be more easily explained at the capillary level than at the level of larger blood vessels. The Capillary Gate hypothesis might also offer an improved explanation of the Blood Brain barrier(63) and cerebral autoregulation(64-66).

Witte et al(67) have demonstrated microvascular endothelial receptor sites for fibrinogen, fibronectin, and Factor VIII, suggesting that these are structural elements of the Capillary Gate Mechanism. Since insoluble fibrin contains fibronectin, I hypothesize that fibronectin receptor sites may actually serve as attachment sites for insoluble fibrin. I hypothesize that the Capillary Gate Mechanism is regulated by the blood level of Factor VIII, as determined by the activity level of the Sympathetic Nervous System. Rising levels of Factor VIII cause increased blood levels of thrombin, which cause elevated levels of insoluble fibrin, whereupon both Factor VIII and insoluble fibrin act in concert with fibrinogen to obstruct capillary flow and close the Capillary Gate.

It has been demonstrated that thrombin inhibits the conversion of plasminogen to plasmin(68), and insoluble fibrin contains plasminogen that is an integral part of its structure. I therefore hypothesize that when levels of Factor VIII decline, the resulting decrease in thrombin level allows spontaneous conversion of plasminogen to plasmin, which attacks and dismembers the insoluble fibrin molecule into "fibrin split products". In addition, enzymes such as urokinase and Tissue Plasminogen Activator (TPa) may attack insoluble fibrin and prevent closure of the capillary gate in certain tissues where uninterrupted capillary perfusion is vital, such as brain and heart tissue. This might explain the "blood brain barrier" and cerebral autoregulation.

This concept is consistent with the observations of Holemans et al(69) that vasoactive drugs are associated with elevated rates of fibrin turnover, and that "vasodilators" are associated with greater levels of fibrin turnover than "vasopressors". I hypothesize that vasopressors enhance fibrin formation and the closure of the Capillary Gate, while vasodilators enhance the breakdown of fibrin and the opening of the Capillary Gate. These agents may effect changes in systemic vascular resistance, and therefore blood pressure, by manipulating the operation of the Capillary Gate(98).

Angiodysplasia, an age-related bleeding diathesis in which visible damage to capillaries occurs(70), may offer direct evidence of a Capillary Gate Mechanism. Angiodysplasia has been shown in all studied forms to be associated with damaged or absent VWF(71-73). It occurs in von Willebrand's Disease(74). It also occurs in uremia(75), aortic stenosis(76-78), and Idiopathic Hypertrophic Subaortic Stenosis(79,80), all of which have been shown to be associated with functional abnormalities of the VWF molecule(81). In the absence of adequate levels of functioning VWF, the half-life of the VIIIC component of the Factor VIII complex becomes undetectable, so that severe defects in the quality or quantity of VWF results in complete cessation of all aspects of Factor VIII complex activity. In contrast, angiodysplasia does not occur in classical hemophilia, where only VIIIC is absent, and normal levels of VWF are present. This suggests that the VWF portion of the Factor VIII complex plays a dominant role in Capillary Gate function compared to the VIIIC component, and defects in the quality or quantity of VWF cause a structural defect in the Capillary Gate Mechanism so severe as to result in visible capillary damage known as angiodysplasia.

Fibrin "cuffs" and deposits have been noted at the entrance and in the lumen of capillaries in association with venous obstruction(82,83). Fibrin deposits in blood vessels and tissues and hyper-elevations of blood coagulability are consistently observed in association with severe stress states(84). These observations are consistent with hyper-elevations of blood fibrin levels that commonly occur in states of stress. I hypothesize that severe stress may cause overproduction of insoluble fibrin that normally functions to close the Capillary Gate Mechanism and regulate blood coagulability, with the result that excess fibrin accumulates at the entrance of the capillary gate and deposits on vessel walls, as in DIC.

Sielenkamper et al have demonstrated unexplained increases in bowel capillary flow in association with epidural anesthesia, despite lowered systemic blood pressure. Kabon et al have demonstrated increased tissue oxygenation associated with epidural anesthesia(85), again despite lowered systemic blood pressure. Kapral et al have demonstrated higher pH in bowel tissue associated with epidural anesthesia(86). Epidural anesthesia has been associated with reduced thrombophlebitis, reduced blood loss(87), increased stroke volume, decreased systemic vascular resistance(88) and overall improvement in morbidity and mortality in high risk patients (89,90). These studies are consistent with the hypothesis that epidural anesthesia may interfere with the systemic release of Factor VIII(91) by decreasing SNS tone and activity levels, thereby reducing blood levels of insoluble fibrin, preventing closure of the Capillary Gate, and improving capillary bed perfusion.

Sielenkamper et al have also demonstrated unexplained decreases in bowel capillary flow in association with sepsis, a powerful cause of stress(92). Sepsis is known to cause stressful effects and elevations in blood levels of Factor VIII(93). The observed decreases in capillary flow may be explained by closure of the Capillary Gate caused by sepsis-induced elevated levels of Factor VIII(94,95).

Luostarinen et al demonstrated unexplained injury-induced decreases in adjacent (uninjured) bowel capillary flow that was restored by direct application of lidocaine(96). The decreases in capillary flow may be explained by the activities of Factors VII and VIII in the vicinity of injury. I hypothesize that the direct application of lidocaine to capillary beds may block the function of exposed SNS nerve endings that terminate in the capillary endothelium, and prevent the release of Factor VIII, thereby opening the Capillary Gate and restoring of capillary flow.

Weinberg et al(97) have demonstrated that bupivacaine inhibits the accumulation of acidic products of anaerobic glycolysis during ventricular fibrillation (VF) in dogs, whereas tissue oxygen levels are not affected. They could not explain this. Like lidocaine, intravenous dosage with bupivacaine may interrupt the function of exposed nerve endings in the vascular endothelium so as to inhibit the release of Factor VIII and prevent the closure of the Capillary Gate Mechanism. This might promote capillary perfusion or diffusion during VF, and thereby mitigate the accumulation of acidic metabolic products in cardiac tissue(98) during VF. Oxygen levels would be expected to be depleted rapidly regardless of the effects of bupivacaine, as VF would interrupt the transport of oxygen via systemic circulation, causing cardiac tissue to rapidly deplete oxygen stores and revert to anaerobic glycosis metabolism, which exaggerates the production of acidic metabolic products.

Anaphylactic shock may also provide insights to Capillary Gate structure and function. It differs from other forms of shock(99) in that it is not associated with elevated fibrin levels or decreased cardiac output. It is characterized by severe hypotension, hives and angioneurotic edema that may cause swelling of airway tissues so severe as to cause death. It is associated with repeated exposure to antigenic drugs and chemicals, notably protamine and bee venom. It can be successfully treated with epinephrine, which is known to cause the release of Factor VIII and to enhance the conversion of fibrinogen to insoluble fibrin(100). I hypothesize that the cause of anaphylaxis symptoms may be a to sudden, widespread failure of the Capillary Gate Mechanism that causes a severe translocation of red cells and plasma from large blood vessels to capillaries and extravascular space. Such a phenomenon might occur if the immune system were to attack one of the Capillary Gate components in association with exposure to antigen, causing sudden, widespread failure of the Capillary Gate mechanism. Existing studies suggest that anaphylaxis may involve sudden a complement-mediated attack on the VWF molecule(101) followed by activation of plasminogen, causing widespread destruction of the insoluble fibrin molecule(102) as thrombin levels fall in response to the inactivation of VWF. These studies are consistent with the hypothesis that insoluble fibrin and VWF are important structural components of an existing Capillary Gate Mechanism.

FIG. 2 shows a diagram of the mechanism of the Capillary Gate.

Thrombin

Serine protease thrombin is a powerful, multifunctional and ubiquitous stress enzyme that plays a central role in coagulation(103-107), DIC(108), injury(109), inflammation (110,111), blood vessel repair(110),and tissue remodeling (21,112,113). Thrombin mediates embryological cell proliferation and tissue development, as evidenced by serious birth defects that occur with fetal exposure to anti-thrombin medications. It inhibits apoptosis(18). Declines in thrombin levels may therefore explain the apoptosis that plays an important role in both embryological development and wound healing (114). Thrombin is routinely employed in the operating theatre to control bleeding from cut surfaces. It mediates platelet activation and fibrin deposition(115). It stimulates fibroblast metabolism, proliferation, hypertrophy(116), and collagen production as an integral part of wound healing(117). It supports and promotes malignancy(118). Thrombin may activate leukocytes, polymorphonucleocytes, monocytes, macrophages and endothelial cells as part of the inflammatory process. It stimulates angiogenesis(118,119). It has been associated with abnormal proliferation of vascular smooth muscle cells and pathogenic vascular remodeling(120). Chronic hypoxia, chemical exposure, and other forms of stress, may induce thrombin-mediated pathological forms of tissue proliferation (17,121). Thrombin may mediate cellular and tissue hypertrophy such as muscular hypertrophy that occurs with mechanical stress to muscles. Its mitogenic effects appear to be inhibited by glucocorticoids, and this may explain certain therapeutic effects of these agents(122).

Thrombin generation appears to depend on the presence of Calcium and Factors VIII and IX(123,124). During the coagulation process, thrombin enzymatically cleaves fibrinogen into fibrin "monomers" that polymerize into strands ("soft" fibrin). It simultaneously catalyzes the activation of Factor XIII ("fibrin stabilizing factor"), which forms fibronectin(125) cross-links in the developing fibrin structure so as to produce a three-dimensional fibrin "matrix" structure known as "insoluble" fibrin(126). Thrombin directly induces platelet activation and platelet elaboration of thromboxane, causing vasoconstriction and reduced blood flow in the immediate vicinity of activated platelets.

I hypothesize that Thrombin stabilizes the plasminogen that is incorporated into the fibrin matrix and prevents it from spontaneously converting to plasmin, thereby preventing plasmin from attacking the fibrin matrix and reducing it to "fibrin split products" (68). Elevated levels of thrombin may thus preserve the integrity of the "insoluble" fibrin structure, which appears to spontaneously disintegrate when levels of VIIIC and thrombin decline. This may explain the ability of VIIIC to control the Capillary Gate Mechanism by regulating thrombin levels.

I hypothesize that these seemingly disparate effects of thrombin are mediated via a common mechanism that is presently obscure. I hypothesize that thrombin is the primary effecter enzyme of the stress mechanism. It is activated by both Factor VII and the VIIIC component of Factor VIII complex and appears to control both coagulation and wound healing.

Often the effects attributed to thrombin have also been attributed to other enzymes. For example, direct platelet activation has been attributed to Factor VIII, collagen, Factor VII and other platelets as well as thrombin. For the sake of simplicity, I assume that in the absence of evidence to the contrary, any effects attributed to both thrombin and another factor are directly caused by thrombin unless proven otherwise, and that the other factors operate indirectly by activating thrombin.

Fibrin, Fibrinogen, and Fibronectin

It is generally accepted that there is a "dynamic equilibrium" in the blood between the forces of coagulation and anti-coagulation, but the exact nature of this equilibrium has never been described(127-129). To explain this, I hypothesize that a homeostatic equilibrium exists between fibrinogen and fibrin that is governed by the opposing effects of Factor VIII and plasminogen(130). Factor VIII acts via thrombin to convert fibrinogen to fibrin and cause elevations in blood levels of insoluble fibrin, but plasminogen rapidly converts to plasmin when blood levels of Factor VIII decline, and then the plasmin attacks and dismantles the "insoluble" fibrin matrix. The dismantling process typically causes elevations in "Fibrin Split Products" or d-Dimers, which appear to be remnants of insoluble fibrin and are associated with increased risk of cardiovascular disease(131,132). In addition to this basic mechanism of fibrin formation and spontaneous self-destruction, there appear to be independent mechanisms governing fibrinolysis, that involve urokinase, tissue plasminogen activator (TPA) and activated Protein C(133). These mechanisms may serve to prevent the closure of the Capillary Gate mechanism under various circumstances.

Thrombin causes the conversion of fibrinogen to "insoluble" fibrin. "Insoluble" fibrin is a three-dimensional structure that appears to incorporate fibronectin, a glycoprotein present in the blood. The conversion of fibrinogen to insoluble fibrin requires some five minutes or more in a test tube; but I hypothesize that it may occur in vivo in a matter of moments(134,135). According to Ellison and Jobes(136) "Native fibrinogen (molecular weight 343,000 daltons) is composed of three pairs of non-identical peptide chains (Aa2, Bb2, Gamma 2) stabilized by disulfide bonds. These are the fibrin monomers. To accomplish the conversion of fibrinogen to fibrin, thrombin catalyzes the cleavage of fibrinopeptides A and B from the Aa and Bb chains, yielding the a and b chains of the fibrin monomer, which polymerize into lengthening strands to yield a soluble form of fibrin. Thrombin then catalyzes the activation of the fibrin-stabilizing factor (Factor XIII), which catalyzes the formation of intermolecular crosslinks between the gamma chains (forming gamma-gamma dimers), and between the a chains (forming a-a multimers)". Fibronectin may be incorporated into this three-dimensional cross-link structure to form a "matrix" structure. Studies demonstrating coagulopathy related to defects in the quality or quantity of Factor XIII illustrate the importance of the cross-linked, three-dimensional form of "insoluble" fibrin (137).

I hypothesize that "insoluble" fibrin, a very large three-dimensional molecular structure, possesses unique physical properties that enable it to simultaneously induce 1. closure of the Capillary Gate Mechanism and 2. increases in blood viscosity, which decreases turbulence and mixing, and thereby increases blood coagulability so as to control the coagulation process.

So-called "soft" fibrin, which consists of fibrin strands that lack cross-links, is present in classical hemophilia, where the VIIIC component of the Factor VIII complex is absent, and "insoluble" fibrin is not produced in appreciable amounts due to the resulting defect in thrombin production and Factor XIII activation. This suggests that the critical defect in hemophilia is the inability to convert "soft" fibrin to "insoluble" fibrin in functional quantities. The resulting inability to regulate blood coagulability and capillary hemostasis may explain the bleeding diathesis that occurs in both hemophilia and von Willebrand's Disease.

Fibronectin is a glycoprotein (disulfite-bonded dimer of 200-220 Kd subunits) that appears to be secreted by the vascular endothelium into blood. It is also found in an insoluble fibrillar form as a component of connective tissue matrix like collagen (proteoglycans) and forms molecular complexes with collagen, fibrinogen, fibrin, heparin, activated factor XIII, and bacteria to form "domains" or subunits, and thus mediate adhesion of cells to cells or cells to biomaterials or tissue and cell migration, chemotactic activity, and tissue stromal organization. It also interacts with hemostatic (138) and fibrinolytic systems and is a part of the fibrinous blood clot. It plays an important role in wound healing and the formation of immune complexes. Depletion of fibronectin due to hyper-activation of the stress mechanism in sepsis (139) may worsen outcome(125), and fibronectin replacement may be an effective treatment(140). In eclampsia, increased circulating levels of fibronectin and Factor VIII are associated with glomerular endotheliosis and hypertension (141).

Calcium, and possibly an external source of energy(142), may be essential for the conversion of soluble fibrin to insoluble fibrin matrix. Calcium appears to be elevated in association with thrombin activity, and elevated Ca+ is also associated with the inhibition of plasmin action. Sodium citrate inhibits clot formation by absorbing calcium; the addition of Ca+ to citrated blood restores the clotting process. Calcium has been used to achieve therapeutic hemostasis (143,144)and sodium citrate has been used to control coagulation in hemodialysis(145).

Plasmins dissolve fibrin, yet small quantities of plasminogen (the plasmin precursor) are adsorbed onto fibrin at lysine-binding sites—thus becoming an integral part of the "insoluble" fibrin matrix(138,146). The fact that both plasminogen and plasminogen activators are incorporated into the fibrin matrix suggests the presence of a mechanism for causing a rapid dissolution or "self destruction" of the fibrin matrix that must somehow be inhibited—otherwise the fibrin structure would be inherently unstable(130,147). As noted previously, this may be explained by the inhibition of plasminogen by thrombin.

Amyloidosis

Numerous clues suggest a direct relationship between fibrin split products (FSP) and amyloid protein. Like FSP, Amyloidosis is associated with excessive fibrin "turnover" in the presence of elevated levels of urokinase(148) and amyloidosis is associated with atherosclerosis(149,150). Amyloid protein appears to interfere with coagulation by competing with fibrin precursors(151-153), particularly Factor X(154), suggesting a structural similarity between FSP and amyloid protein. Like fibrin, amyloid protein appears in the form of chains or fibrils. Fibronectin, a component of insoluble fibrin, and vitronectin, a component of amyloid, are both glycoproteins, and may be closely related(155). Both fibrin breakdown products and amyloid appear to be associated with hypercoagulability states(156) and both interfere with coagulation(157-160); they may be directly related. Like fibrin, amyloid protein tends to appear as deposits in vessels (161) and organ tissues in association with stressful conditions(152,162,163) and this may be a largely unappreciated source of pathology(151,164). Occult amyloid deposits that damage blood vessels and surrounding tissues may be a factor in Congestive heart failure(164) and ischemic colitis(160). Amyloid protein appears in rheumatoid nodules(165) and in the synovium(166) and other tissues (167-170)of patients afflicted with rheumatoid arthritis and other rheumatoid diseases(171). Amyloid may be a cause or a contributing factor in the development of diabetes, a stress-related condition (172), and Alzheimer's Disease(l173).

On the basis of this evidence, I hypothesize that amyloid protein is a form of "fibrin split products" or d-dimer that has undergone a conformational change that renders it distinct (174). Amyloid protein and fibrin degradation products may represent the "exhaust" produced by the operation of the Capillary Gate Mechanism, and increased blood levels of these proteins may be caused by opening and closing of the Capillary Gate Mechanism by urokinase, vasoactive drugs or stress-related factors. I further hypothesize that rheumatoid diseases represent clinical manifestations of amyloidosis (175-178).

Factor VIII

The "classical" hormonal response to trauma is described as activation of the hypothalamic-pituitary-adrenal axis and the sympathetic nervous system interacting with immunological responses(179). Neither Factor VIII nor Factor VII has been previously associated with this concept, but their proposed roles in Stress Theory may offer an improved explanation of the known effects of stress(180). I hypothesize that Factor VIII is a stress hormone that is secreted directly into systemic circulation under Sympathetic Nervous System control by the vascular endothelium, a gland. It is released into circulation in circumstances similar to those in which other stress hormones, such as epinephrine, glucagon, and cortisol are released. Its function is to regulate the activity level of the Stress Mechanism including systemic blood coagulability and Capillary Gate closure, and synergize with the localized effects of Factor VII, a companion stress enzyme, to induce localized hyper-elevations of thrombin that initiate coagulation and regulate wound healing at the site of injury or stress. Factor VIII may be elevated in response to either psychic or somatic pain and stress or both, as well as other forms of stressful stimuli that increase SNS activity levels(181). It may thus be released pre-emptively prior to actual injury so as to minimize blood loss, as part of the "fight or flight" stress mechanism described by Hans Selye.

Factor VIII consists of two very large molecules, VIIIC and VWF(182). These circulate together and exert their effects in concert. Unlike other known coagulation proteins that are produced in abundance by the liver and have prolonged, stable half-lives, Factor VIII is produced in the vascular endothelium, normally has a brief half-life of some 3-5 hours, and both its half-life and blood levels fluctuate constantly in association with a wide variety of stressful diseases and stimuli(183-186). For example, blood levels of Factor VIII correlate with the severity of DIC,(187) eclampsia(188) and Raynoud's syndrome(189).

Decreases in Factor VIII are associated with lowered blood viscosity and coagulability. Increases in Factor VIII are associated with increases in blood coagulability, in blood viscosity, in platelet activation, and in stress-related symptoms (190). Its effects appear to be largely attributable to regulation of thrombin levels(191). Both the half life and blood levels of Factor VIII constantly fluctuate in accord with SNS tone and activity levels and hypothalamic stimulation. Blood levels of Factor VIII appear to decline after anesthesia induction and ablation of psychic stress, accompanied by decreases in blood coagulability and viscosity, but then rise progressively with the onset of surgical tissue disruption. Blood levels of Factor VIII may remain elevated for at least eight days after surgical procedures, causing increases in blood coagulability, inflammation, and increased incidence of stress-related symptoms (192,193).

Manucci et al first demonstrated that Factor VIII is released under nervous control in response to somatic pain(194). Several studies have associated pure psychic pain and stress, such as fainting(195) or experiencing an earthquake without injury, with sharp elevations in Factor VIII and fibrin(196) as well as increased incidence of myocardial infarction, stroke, and angina, all of which are stress-related (51,197,198). Blood levels of Factor VIII may exhibit very sudden but short-lived increases, such as those following hard muscular exercise, fainting, or the injection of adrenalin; they may exhibit sustained changes, such as those observed in pregnancy, diabetes, sepsis, inflammatory states, hyperthyroidism (199) and other stress-related conditions. Starvation depresses both SNS activity and Factor VIII levels(200,201), as does myxedema(202) and moderate alcohol consumption.

Hypothalamic stimulation, which is known to control SNS activity levels, can cause either increases or decreases in Factor VIII blood levels, depending on the part of the hypothalamus being stimulated(203,204). Hypothalamic stimulation has also been shown to cause endothelial damage and to accelerate atherosclerosis(205-208).

The VIIIC component of the Factor VIII complex is sex-linked, as the gene that produces it is located on the X chromosome. It mediates the conversion of prothrombin to thrombin, thereby activating the various effects of thrombin. The inherited inability to produce VIIIC is the cause of true hemophilia, which afflicted the royal families of Europe.

VWF is produced by a somatic gene. It stabilizes VIIIC and extends its half-life. In the complete absence of VWF, the half-life of VIIIC is so short as to be undetectable, resulting in a bleeding diathesis that cannot be distinguished from true hemophilia. VWF is known to facilitate the adhesion of platelets to fibrinogen, fibrin, fibronectin, exposed collagen, and to one another so as to facilitate the formation of white thrombi ("white clots") as a prelude to "red" clot formation(209). I hypothesize that this is explained its ability to enhance and prolong VIIIC activity, thrombin production and Factor XIII activation. Defects in the quality or quantity of VWF may result in bleeding problems known as "von Willebrand's Disease" that vary widely in severity, presumably due to simultaneous impairment of both VWF and VIIIC function. As noted previously, VWF may be a major factor in the operation of the Capillary Gate Mechanism.

I hypothesize that the stabilizing role of the VWF component of Factor VIII complex automatically extends the half-life of Factor VIII when large quantities of Factor VIII are released. This has important implications for the control of inflammation and the stress syndrome because it implies that once significant amounts of Factor VIII are released, Stress Mechanism activity may remain elevated regardless of subsequent stress-control measures and restoration of normal SNS activity levels. This may explain the beneficial effects attributed to pre-emptive anesthesia(210), and explain much of the confusion that has bedeviled research on the subject of stress.

Shear Stress, Turbulence and Mixing

Turbulence and mixing in the blood have long been suspected of playing a role in both coagulation and atherosclerosis, but a clear explanation of how this might occur is lacking. Arterial blood flow appears to operate near a "transition zone" where small increases or decreases in shear stress (the force associated with the forward movement of blood) result in large increases in turbulence and mixing(211). The cardiac cycle induces two peaks of turbulence in arterial blood flow(50). The first occurs in mid-systole, at the time of maximum shear stress. The second occurs in mid-diastole, when blood flow momentarily reverses direction.

Turbulence is enhanced by hyperdynamic cardiac function, such as athletic activity, and depressed by hypodynamic cardiac function such as occurs in congestive heart failure. This is consistent with the observation that athletic conditioning retards atherosclerosis(212) and hypodynamic heart function or low activity levels such as found in obesity, congestive heart failure and myxedema are associated with accelerated atherosclerosis. The effects of turbulence and mixing are also consistent with the observation that thrombophlebitis rarely occurs in arteries, but is not uncommon in areas of stasis in the venous system, especially in the presence of hypercoagulability and hyperviscosity of blood, where levels of turbulence and mixing are reduced.

Bjorn Hof et al recently published studies of fluid flow in pipes that demonstrate sharp increases in turbulence and mixing associated with sudden acceleration of flow rates(213). These studies, which employed laser beams and cameras to track microscopic tracer beads in water, demonstrated that a sudden increase in water flow rate in a pipe resulted in turbulent vortices that pushed sluggish water to the center of the pipe, creating a slow-moving streak down the center and fast-moving streaks around it. These studies suggest that pulsatile blood flow induces sharp increases in turbulence and mixing that occur most prominently along the walls of blood vessels in association with sudden increases in shear stress induced by cardiac activity. Such turbulence and mixing might play an important role in preventing the deposition of blood elements on vessel walls and inhibiting coagulation.

Wettstein et al(137) have demonstrated that defects in the quantity or quality of coagulation factor XIII causes bleeding problems. Factor XIII governs the formation of fibronectin cross-links to form a three-dimensional fibrin structure. I hypothesize that the physical properties of this three-dimensional structure induce "damping" of turbulence and mixing in blood, and its absence may disable the coagulation mechanism. Kawasaki et al (214)have demonstrated how fibrin strands, visible on electron micrographs, form attachments among various blood components as an integral part of the coagulation process. These attachments may also induce "damping" of turbulence and mixing in blood, or synergize with the damping effects of three-dimensional fibrin matrix. Alexandrov et al(215) have demonstrated that ultrasound may inhibit blood clot formation and disrupt existing blood clots. Ultrasound may exert these effects by increasing turbulence and mixing in the blood.

DESCRIPTION OF THE PREFERRED EMBODIMENT(S)

Figure 1:
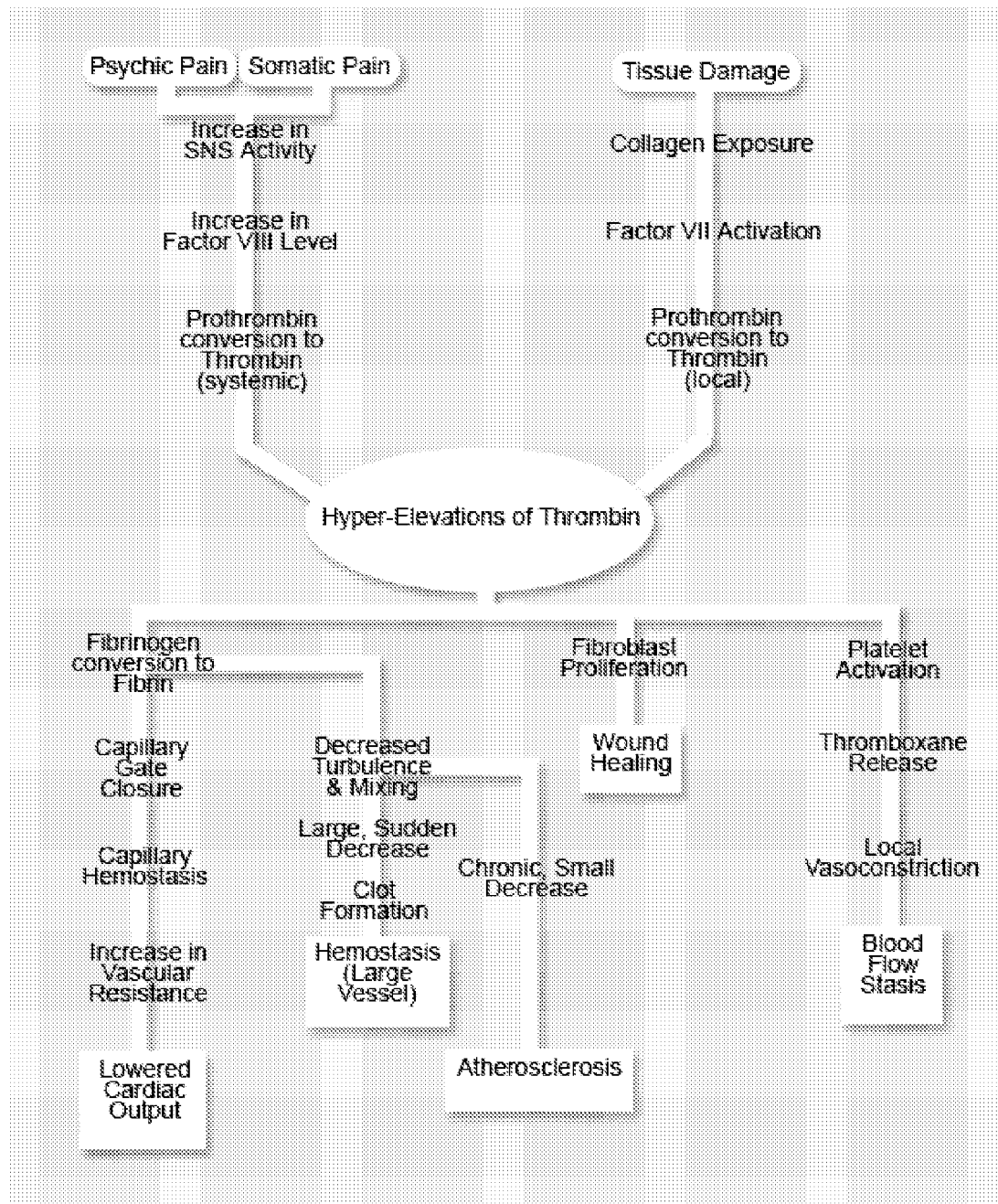
FIG. 1 is a diagram showing the effects of hyper-elevations of thrombin.
Figure 2:
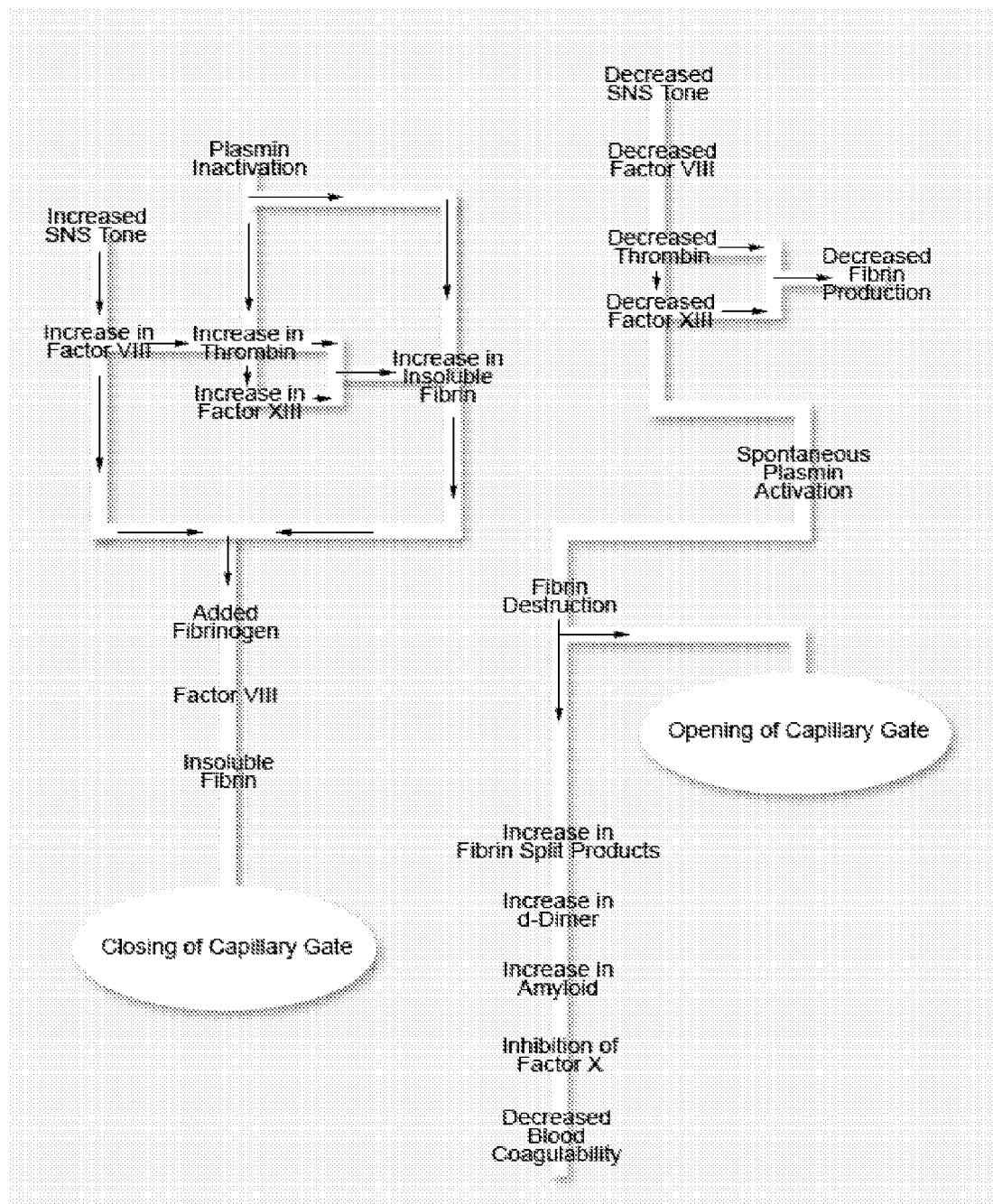
FIG. 2 is a diagram showing the events leading to, respectively, closing and opening of the capillary gate

The detailed description set forth below in connection with the appended drawings is intended as a description of presently-preferred embodiments of the invention and is not intended to represent the only forms in which the present invention may be constructed and/or utilized. The description sets forth the functions and the sequence of steps for constructing and operating the invention in connection with the illustrated embodiments. However, it is to be understood that the same or equivalent functions and sequences may be accomplished by different embodiments that are also intended to be encompassed within the spirit and scope of the invention.

I hypothesize that blood turbulence and mixing induced by pulsatile blood flow, which is associated with sharp increases in mixing, inhibits blood coagulability by preventing blood components from adhering to one another to form clots. I likewise hypothesize that turbulence and mixing inhibits atherosclerosis by preventing toxic blood components from escaping suspension in the blood and depositing on arterial surfaces and initiating the inflammatory response that results in atheroma formation.

Viscosity

In fluid dynamics, turbulence and mixing vary inversely with viscosity. I hypothesize that chronic increases in blood viscosity, which may be caused by various factors, causes damping (decrease) of blood turbulence and mixing that accelerates atherosclerosis by allowing toxic blood components to escape suspension in the blood and form deposits on arterial walls that cause atheroma(216,217). I hypothesize that acute, localized hyper-elevations of blood fibrin levels under the combined control of Factors VII and VIII cause localized increases in viscosity, resulting in decreases in turbulence and mixing that enable blood clot formation. When the fibrin matrix damps turbulence and mixing below a critical threshold, fibrin strands form spontaneously and connect various blood components to one another so as to induce even greater increases in viscosity and decreases in turbulence and mixing. As turbulence levels fall, additional fibrin strands form spontaneously and connect blood components into a clot. I hypothesize that extreme systemic hyperviscosity of the blood that causes systemic decreases in turbulence and mixing is the cause of DIC(218,219). Blood viscosity appears to be determined by a combination of factors primarily including the following:

1. Levels of the three-dimensional form of "insoluble" fibrin that are systemically regulated by Factor VIII.
2. Levels of fibrinogen, which are normally stable and genetically-controlled, but may be elevated in chronic stress conditions such as smoking syndrome or diabetes(220,221).
3. Red cell mass,(222-224) as elevated in polycythemia vera (225); excessive erythropoiten(226); excessive transfusion with washed, packed RBC's(227); or as decreased in conditions such as the anemia of chronic uremia(228,229) or iatrogenic hemodilution.(230,231)
4. Disease states such as leukemia or multiple myeloma(232), in which a profusion of white cells or immune globulin proteins cause increases in viscosity(233,234).
5. Hyperlipidemia(235)

Elevations of blood viscosity caused by any of these factors, or combinations of these factors, may pre-dispose a patient to problems associated with hypercoagulability, such as thrombophlebitis(236,237), accelerated atherosclerosis, and impaired capillary perfusion(217,238). Blood transfusions may cause elevations in blood viscosity(239) and excessive transfusion of packed red blood cells can cause a form of DIC. Extreme stress-related elevations in blood viscosity due to abnormal elevations in blood levels of insoluble fibrin, such as those associated with sepsis(240), trauma(241), prolonged surgical procedures, or the hemolysis elevated liver enzymes, and low platelet count syndrome (hereinafter "HELLP Syndrome") of eclampsia, are known to precede and pre-dispose to the onset of DIC syndrome(242-244), in which spontaneous widespread coagulation occurs(218,245,246). Over-transfusion with washed, packed red blood cells produces a similar situation.

Low blood viscosity states, such as those found in anemia caused by uremia or by acute blood loss and iatrogenic hemodilution, may exaggerate blood turbulence and mixing and thereby inhibit blood coagulability so as to aggravate bleeding tendencies. This may provide a better explanation than the "platelet washout syndrome" to which bleeding problems associated with massive blood loss, hemodilution and uremia(247) are commonly attributed.

Atherosclerosis

Atherosclerosis is widely blamed on elevated blood levels or intake of cholesterol or lipids, but the evidence for this is questionable(248,249). It correlates with advancing age, sedentary life style, hemodynamic stress(250), increasing blood levels of Factor VIII(251), increases in blood viscosity(222), elevated fibrin(131)and fibrinogen levels(252) and hypercoagulability(253,254), all of which are associated with increased blood viscosity. Anemia lowers blood viscosity and inhibits atherosclerosis, whereas elevated hematocrit accelerates it(222). Stressful diseases such as hyperthyroidism, which elevate blood viscosity, are associated with accelerated atherosclerosis despite normal or increased cardiac output (255,256) and shear stress. Hypodynamic cardiac function, as in congestive heart failure and myxedema(257) is associated with accelerated atherosclerosis(258). Most chronic diseases are associated with accelerated atherosclerosis(256).

Atherosclerosis is opposed by athletic conditioning(259), which increases turbulence and mixing. Several studies have demonstrated that moderate alcohol consumption, such as a glass of red wine every evening, retards atheroma formation and cardiovascular disease(260). The sedative effects of alcohol may reduce psychic stress, and reduce blood viscosity. There is evidence that atherosclerosis may be retarded by hemophilia and von Willebrand's Disease(261,262), though these patients retain the ability to heal wounds and form scabs. This may be explained by the inability of these patients to produce the cross-linked form of fibrin.

The observation that atheroma formation begins on the greater curvatures of the bifurcations of arteries, where shear stress is decreased(263), has led to the published hypothesis that low shear stress is the cause of atherosclerosis(211,264, 265). The shear stress hypothesis explains most of the facts noted above, but is deficient in important respects. For example, it fails to explain the acceleration of atherosclerosis that occurs in stressful conditions such as hyperthyroidism or direct hypothalamic stimulation, where both cardiac output and shear stress are maintained or increased. It also fails to explain the observation that regular, moderate alcohol consumption, which is associated with low levels of shear stress, retards atherosclerosis.

I hypothesize that atherosclerosis is inhibited by blood turbulence and mixing, as opposed to shear stress. Low shear stress and low turbulence and mixing tend to occur under similar conditions; however, shear stress is minimally affected by viscosity, whereas turbulence and mixing may be sharply inhibited by elevations in viscosity, and enhanced by reductions in viscosity. This would better explain the accelerated atherosclerosis that occurs in stressful conditions, such as hyperthyroidism(266), where the turbulent effects of hyperdynamic heart function may be negated by elevations in is Factor VIII, which increases blood viscosity by causing elevated levels of three-dimensional fibrin matrix in the blood. It would also better explain how the tranquilizing effects of moderate alcohol consumption retard atherosclerosis by decreasing psychic stress and SNS activity levels, and lowering blood levels of Factor VIII, insoluble fibrin, and blood viscosity(267).

Smoking Syndrome

Somewhat surprisingly, Smoking Syndrome does not appear to be associated with elevated levels of Factor VIII and insoluble fibrin(268), though it is associated with other stress-related illnesses and may exaggerate their incidence or severity(37,269,270). However, it is consistently associated with elevated levels of blood fibrinogen(220,271), platelet reactivity(272), red cell mass, and blood viscosity(273). I hypothesize that smoking induces increases in blood viscosity by increasing both red cell mass and blood fibrinogen(274) levels, and that the increased viscosity causes decreased turbulence and mixing in the blood, which is responsible for the acceleration of atherosclerosis and heart disease that is strongly associated with Smoking Syndrome(275,276).

Nicotine is known to have powerful sedative/hypnotic and stress-opposing effects(277). I hypothesize that it reduces psychic stress and thereby reduces blood levels of Factor VIII, thereby possibly explaining the normal levels of Factor VIII observed in smokers. The effects of nicotine may oppose and offset the otherwise stressful effects of smoking. This is consistent with the observation that smoking reduces the severity of symptoms in eclampsia, where the tranquilizing effects of nicotine may reduce Factor VIII levels and blood viscosity. The effect may be similar to the protective effect of moderate alcohol consumption(260,267). These sedative effects in and of themselves may mitigate the release of Factor VIII and help prevent acute increases in blood viscosity due to fibrin matrix, but the chronic increase in blood viscosity caused by elevated hematocrit and fibrinogen may dominate the beneficial effects of nicotine.

Factor VII, Coagulation, Wound Healing and Apoptosis

A substance or a mechanism has long been suspected but never verified that localizes and controls the inflammatory response, "white clot" and subsequent "red clot" formation, fibroblast proliferation, and wound healing(278). Factor VII is known to be activated by exposed collagen, and to cause conversion of prothrombin to thrombin(279). It is known to activate the "intrinsic" pathway(280). I hypothesize that Factor VII is a locally-acting stress agent that synergizes with the systemic effects of Factor VIII to cause hyper-elevations of thrombin at the site of tissue disruption and thereby govern localized clot formation and wound healing(281).

I hypothesize that "tissue factor" is collagen or a portion of the collagen molecule(16,282-285). Collagen, a ubiquitous protein that is a basic structural component of all larger blood vessels, is normally separated from flowing blood by the delicate vascular endothelium, which is only one cell layer thick(286). Traumatic stress that disrupts the vascular endothelium immediately exposes underlying collagen to flowing blood and activates Factor VII.

Factor VII has been successfully employed via intravenous infusion as a substitute for Factor VIII to treat hemophilia (287,288) and trauma(289) but its normal thrombin-elevating effects are believed to be primarily local, whereas those of Factor VIII appear to be systemic(49). Like Factor VIII, the half-life of Factor VII is very short, and it must be administered as an infusion to treat hemophilia(290). Its origin appears to be hepatocytes(291), and its function is vitamin K dependent. Like Fibrinogen, its blood level is normally stable and genetically controlled, but may be elevated in chronic stress conditions such as diabetes(292). If administered in excessive quantities, it causes hypercoagulability of blood, as also occurs with Factor VIII. Deficiencies in the quality or quantity of Factor VII are rare but devastating(293,294).

Normally, thrombin elevation by both Factor VII and Factor VIII is required for effective clot formation. In rare circumstances, such as severe sepsis or eclampsia, extreme stress-related elevations in Factor VIII may cause severe systemic hypercoagulability that pre-disposes to DIC; however, with the exception of venous thrombophlebitis, the hypercoagulability induced by Factor VIII is not ordinarily associated with clot formation in the absence of tissue disruption and Factor VII activation. Likewise, in the absence of Factor VIII, Factor VII does not appear to be produced in adequate quantities to initiate clot formation, as evidenced by the absence of clot formation in hemophilia(295). Normal coagulation appears to involve the combined effects of Factors VII and VIII in response to a combination of SNS activation and collagen exposure to flowing blood that elevates local thrombin levels and initiates "white clot" formation and then governs the transition of "white clot" to "red clot" as collagen is repeatedly re-exposed and Factor VII is re-activated.

Subsequent re-exposure of collagen due to deterioration of the "red clot" causes persistent re-elevations of thrombin levels at the site of injury that initiate and sustain the inflammatory response, fibroblast proliferation and collagen production, and thereby govern the wound-healing process(130). Factor VII may also control cell migration(296) via thrombin. As wound healing proceeds to completion, collagen is ultimately sealed from exposure to flowing blood, thrombin levels decline, and the acute phase of wound healing ends. I hypothesize that apoptosis is caused by declining thrombin levels that occur during the resolution of the acute phase of the wound healing process(18,19). That Factor VII plays a major role in regulating the wound healing process is consistent with the fact that wound healing and scab formation appear to remain near-normal in the absence of Factor VIII(297).

It is known that proliferating fibroblasts are exquisitely sensitive to hypoxia and acidosis, which may cause inadvertent apoptosis, and that the early stages of capillary formation that take place in the wound healing process may be disrupted by a variety of stressful stimuli(278). This may explain the poor wound healing and increased incidence of wound infection associated with uncontrolled surgical stress. I hypothesize that proliferating fibroblast cells are inherently fragile and susceptible to apoptosis, and are critically dependent on adequate but not excessive levels of thrombin to multiply and function correctly.

Virchow's Triad and the Coagulation Cascade Theory

More than 150 years ago, Rudolf Virchow stated his famous "Triad" of postulates that must be present in order for blood coagulation to occur: 1. blood flow stasis; 2. hypercoagulability of blood; and 3. tissue crushing. The understanding of how coagulation occurs has changed little since Virchow's time, and the mechanisms of these postulates have yet to be explained.

Although it seems intuitively logical, the "Cascade" theory of blood coagulation is dauntingly complex and confusing, and exhibits numerous shortcomings and inconsistencies. It fails to provide a clear explanation of the postulates of Virchow's Triad. It implies that enzymatic blood proteins engage in a series of confusing and cross-related interactions that culminate in the formation of fibrin, but offers no explanation of how fibrin might control either hemostasis or localized clot formation. It offers few clues as to how so potent a system might cause disease or be affected by it. It fails to explain the perturbations in blood viscosity, coagulability, and rheology that are commonly associated with disease processes. These are but a few of its more obvious shortcomings. Worse yet, many of the laboratory tests that have been used both to study the cascade theory and perform clinical testing are inadequately standardized, indirect in nature or simultaneously test multiple reactions, and thus they may produce confusing or contradictory results. For example, published studies have variously attributed direct platelet activation to thrombin, Factor VIII, Factor VII, and collagen. Inhibition of the conversion of plasminogen to plasmin has been attributed to both thrombin and "Plasmin Activator Inhibitor-1" (PAI-I)(68). Factor VII activation has been confusingly attributed to both exposed collagen and "Tissue Factor," when it would appear that both "Tissue Factor" and collagen are present in the same extravascular location, suggesting that they might be one and the same. The effect of this confusion may be to discourage logical and systematic investigation.

Stress Theory, in contrast to Cascade Theory, may offer a simple explanation of Virchow's Triad, as follows:

1. Injury causes a combination of psychic and somatic pain and stress that cause SNS activation and the release of Factor VIII, causing systemic elevations in thrombin.
2. Disruption of the vascular endothelium (tissue crushing) causes Factor VII activation at the site of injury that produces additional elevations of thrombin in the immediate vicinity of injury.
3. The localized hyper-elevated levels of thrombin due to the combined effects of Factors VII and VIII cause platelet activation and the release of thromboxane, which causes intense vasoconstriction and stasis of blood flow in the immediate vicinity of injury, plus elevations in levels of insoluble fibrin that induce hypercoagulability of blood that results in visible clot formation.

Malignancy

Prevailing theories of the cause of malignancy usually involve the assumption of genetic damage induced by radiation, viruses, or other factors that cause cells to undergo a malignant change. I propose an alternative explanation. I hypothesize that the cause of malignancy is prolonged, stress-related hyper-elevation of systemic and local thrombin levels that over-stimulate wound-healing cell proliferation(298) and cause proliferating wound cells to invade normal tissues and provoke a self-sustaining stress response(296). I hypothesize that the resulting stress response maintains elevated thrombin levels so as to support continued cell proliferation and invasion(282,299). This hypothesis is consistent with the observation that chronic ingestion of toxic chemicals is associated with increased rates of various types of malignancies in various locations, but painting the same chemicals on skin surface causes greater increases in the incidence of cancer at the application site than systemically. It is also consistent with the association between malignancy and stressful conditions such as diabetes and morbid obesity.

Malignancy is known to be associated with sustained and elevated stress, such as prolonged osteomyelitis infection and sepsis, chronic exposure to toxic chemicals, or chronic tobacco abuse. It is increased in the aftermath of major surgery, a stressful event. Cancer is typically accompanied by increases in Factor VIII and thrombin, accompanied by increases in blood viscosity and coagulability(300); the relation may be one of both cause and effect. Thrombin has been demonstrated to promote both mitosis(112) and malignancy (118,301). Thrombin has been demonstrated to stimulate proliferation of brain astrocytes, and may be directly associated with astrocytoma(113,302,303). Thrombin has also been shown to play an important role in lung(304) and colon(305) adenocarcinoma. Elevated levels of thrombin may be necessary for cancer cell survival(114). Elevations of Factor VII also promote malignancy(306). Anti-thrombin medications have been demonstrated to induce apoptosis and enhance the effectiveness of other cancer treatments(114,301), suggesting that a combination of intense anti-stress and anti-thrombin measures might offer an improved means of inducing apoptosis so as to treat malignancy. I hypothesize that conventional cancer therapies, including surgery, chemotherapy, and radiation therapy, are innately counter-productive, in that they cause stressful stimulus that tends to aggravate the malignant process they are intended to cure.

Pharmacology and the Capillary Gate

Stress Theory might offer an improved understanding of the mode of action of vasoactive drugs that are commonly employed as anesthesia adjuncts, and might lead to more judicious use of these agents. The terms "vasopressor," "vasodilator," and "vasoconstrictor" imply that such agents owe their effects to muscular constriction or relaxation of the lumens of arteries, arterioles, veins, and venules. These terms may be misnomers. Stress Theory and research evidence suggests that "vasodilator" drugs such as nitroprusside(307), nigroglycerine(308,309), epsilon-aminocaproic acid (EACA)(310), MgSO4(311-313) and furosemide(314) interfere with the conversion of "soft" fibrin to "insoluble" fibrin, or induce fibrinolysis(69), so as to prevent the closure of the Capillary Gate Mechanism, reduce systemic vascular resistance, and lower blood pressure. The therapeutic effects of these drugs may be explained by their ability to improve capillary bed perfusion. "Vasoconstrictor" drugs such as epinephrine(315), vasopressin(315) and ionized calcium(124) may promote the conversion of "soft" fibrin to "insoluble" fibrin and thereby facilitate closure of the Capillary Gate Mechanism, increase systemic vascular resistance, and thereby increase blood pressure. Thus "vasopressors" may enhance CFS effects, while "vasodilators" may oppose them. This may better explain the mode of action and many of the side-effects associated with excessive use of "vasopressor" drugs.

Calcium channel blockers such as Nifedipine and Verapamil are known to lower blood levels of Ca+, and thus may exert their effects by interfering with the formation of insoluble fibrin. They have been used successfully to treat Raynoud's Syndrome(316). They are known to reduce blood pressure(317), blood viscosity(318) and systemic vascular resistance, and preserve cardiac output(317). They may inhibit atherosclerosis(319) and tissue hypertrophy induced by stress (both effects being mediated by thrombin)(30). They have been associated with bleeding problems(320,321). In contrast, calcium preparations have been used to control bone bleeding. Calcium channel blockers have also been shown to reduce myocardial infarct size in rats(322), augment bowel and myocardial perfusion in shock states(323), prevent the "no-reflow" phenomenon that sometimes follows successful angioplasty procedures(324,325), and are associated with beneficial effects on atherosclerosis. I hypothesize that "no-reflow" is a manifestation of CFS in cardiac tissue. Calcium Channel blockers also appear to interfere with platelet activation. They may exert these therapeutic effects by interfering with the elevation in Ca+ levels associated with thrombin actions(6).

Local anesthetics have well-recognized systemic anesthetic, anti-inflammatory and anti-coagulant effects(326-328). The anti-coagulant effects and anti-inflammatory effects are unexplained. Their anti-arrhythmic effects are presently attributed to their supposed ability to stabilize nervous conduction pathways in the heart. I propose an alternative explanation. I hypothesize that local anesthetics anesthetize the exposed nerve endings of the SNS in the vascular endothelium and prevent the release of Factor VIII. I hypothesize that local anesthetics achieve their anti-arrhythmic actions by reversing CFS and tissue ischemia in nervous, pulmonary(329) and cardiac tissue, thereby restoring is stable function. I hypothesize that the anti-inflammatory and anti-coagulant effects of local anesthetics are likewise explained by inhibition of Factor VIII release, and lowered levels of thrombin activity. When administered via conduction anesthetic techniques, they may block sympathetic nerves directly, also preventing the release of Factor VIII, plus small amounts may escape into systemic circulation and exert additional effects.

Surgeons frequently employ mixtures of local anesthetics and epinephrine to simultaneously control surgical pain and effect hemostasis(330,331). In most cases this approach works well(332), but in certain patients the presence of local anesthetics is associated with persistent "oozing" (333). There have been reports of serious hematoma formation that has accompanied the use of local anesthetic injections of tissues(334). I hypothesize that these occasional manifestations of inadequate hemostasis are caused by mild cases of von Willebrand's Disease, in which the effects of local anesthetics further inhibit the already marginal function of the Factor VIII molecule and prevent closure of the Capillary Gate, thereby causing failure of capillary hemostasis.

Streptokinase and urokinase appear to exert their effects by enhancing the operation of plasmin. Their benefits may derive from their ability to promote the dismemberment of the three-dimensional insoluble fibrin matrix by plasmin, reduce systemic hypercoagulability of blood, and cause opening of the Capillary Gate and reduction of CFS. The sudden hypotension associated with large doses of these drugs may be explained by sudden, widespread opening of the Capillary Gate that causes a decrease in systemic vascular resistance. This may also explain the "re-perfusion arrhythmias" that are associated with these drugs, which may be caused by a "steal" phenomenon of blood flow at the expense of compromised tissues. The therapeutic benefits associated with these drugs may derive primarily from their ability to reverse CFS during the early stages of evolving MI, as thrombosis appears late in the infarction process(52,335).

Beta-blocker drugs such as propranolol are presently believed to exert their benefits by lowering heart rate and increasing diastolic filling time. However, these drugs are also known to interfere with platelet activity(336), lower blood fibrinogen levels(337) and lower blood levels of Factor VIII(315). Thus, the benefits of these drugs may derive primarily from their ability to inhibit the stress mechanism.

Aspirin is presently thought to produce its therapeutic effects by inhibiting platelets. It's inhibition of other elements of the coagulation process are poorly appreciated, and its beneficial effects may derive primarily from its ability to inhibit CFS rather from platelet effects(338).

Stress Syndrome

The "Fight or Flight" Stress Syndrome described by Hans Selye may be explained in terms of stress-related effects (hypercoagulability of blood, capillary hemostasis, increased systemic vascular resistance, elevated blood pressure etc.) that are activated by psychic stress and stimulus and the release of stress hormones, including Factor VIII, in advance of physical injury so as to minimize blood loss in the event of subsequent injury and enhance the success of fighting or escaping. The survival benefits of such a mechanism are self-evident, and abundant evidence exists that SNS activity levels and blood levels of Factor VIII can be elevated by fear and psychological stress, sometimes accompanied by pathological manifestations of stress such as myocardial infarction, stroke and sudden death.

In contrast, the "Surgical Stress Syndrome" may be explained by the inadvertent elevation of SNS activity levels and release of Factor VIII due to inadequately controlled somatic stress despite ablation of the patient's psychic stress and conscious awareness of pain via the use of sedative/hypnotic anesthetic agents. Prevailing techniques for administering general anesthesia ("Traditional" Technique) rely heavily on combinations of inhalation agents and muscle relaxants to achieve satisfactory operating conditions, but these do not inhibit the effects of somatic stress. SNS tone and activity levels, and blood levels of Factor VIII, blood coagulability, platelet activity(192) and viscosity decline on induction of anesthesia and ablation of psychic stress and awareness, but then begin to rise after surgical stimulus and the onset of somatic stress. These do not reach peak levels until several hours after completion of the surgical procedure and do not return to normal levels for at least several days. Psychic stress associated with anesthesia emergence and restoration of the conscious awareness of pain may add to the stressful activation of SNS activity levels caused by tissue disruption. Stress-related morbidity and mortality coincides with the rise in Factor VIII blood levels(339).

Sufficiently activated, Factor VIII levels may remain elevated for at least eight days after surgery, long after SNS activity levels have returned to normal, and these may be resistant to subsequent pain control measures. This prolongation of the half-life of Factor VIII and its insensitivity to subsequent stress-control measures may be explained by the preserving and stabilizing effects associated with the release of large amounts of VWF and/or CNS "Wind-Up". The elevation in Factor VIII levels is mirrored by clinical manifestations of the Surgical Stress Syndrome, including vasomotor instability, tachycardia, hypertension, fever, mental disorientation, stroke, dysrhythmias, myocardial infarction, bowel ileus, poor wound healing, wound infection, and death.

Both the rise in Factor VIII levels and manifestations of surgical stress may be mitigated by the pre-emptive use of conduction anesthesia(340), local anesthetic infiltration, generous dosage with opioids(341), and other stress control techniques(342) that inhibit the release of Factor VIII; however, I hypothesize that any lapse of stress control that allows SNS activation during or for several hours after surgical tissue disruption may risk causing sustained elevations of Factor VIII that may subsequently resist control.

I hypothesize that the pathological effects associated with the Surgical Stress Syndrome are primarily caused by uncontrolled elevations of circulating Factor VIII that cause elevated thrombin activity, hyperviscosity and hypercoagulability of blood, systemic inflammation, and prolonged and widespread closure of the Capillary Gate Mechanism that results in cellular hypoxia and tissue damage in capillary beds—"Capillary Fibrin Stress" (CFS). CFS may explain the increased incidence of stress-related problems in geriatric patients(343), whose decreased cardiac index, increased blood levels of Factor VIII(106,344,345), and senescent capillary beds that have been shown to have perfusion defects (346), may render them more vulnerable to CFS, thrombophlebitis and atherosclerosis than younger patients. It is also consistent with the fact that most stress symptoms are closely associated with vital organs that require uninterrupted perfusion, such as brain, bowel, heart and kidneys.

Prolonged, low-grade activation of the Stress Mechanism after surgical procedures may cause persistent systemic inflammation and explain the increase in malignancy, mortality and morbidity in the distant aftermath of surgery noted by Terri Monk et al(347) that strongly correlates with the "Traditional" technique of general anesthesia that relies primarily on inhalation agents and muscle relaxants and does not effectively inhibit somatic stress.

Anesthesiology and Stress Theory

Stress Theory suggests a new Theory of Anesthesia and alternative anesthetic goals and strategies to optimize surgical outcome. Previous attempts to develop theories of anesthesia that are confined to explaining the reversibility of the conscious awareness of pain may be inadequate. Anesthesia may be analogous to stress control. The optimal role of the anesthesiologist may be to protect his patient from stressful stimulus whenever possible, and to employ adequate doses of analgesics (local anesthetics and opioids) to control the effects of somatic surgical stress in addition to the traditional use of hypnotics to ablate conscious awareness and the effects of psychic surgical stress. Optimal outcome may require pre-emptive, uninterrupted measures to control the effects of both psychic and somatic surgical stress and prevent hyper-activation of the Stress Mechanism. The term "anesthesia" which means "loss of sensation" may be inadequate to describe this role. For lack of a better term, I call this "antinociception anesthesia".

Traditional approaches to anesthesia rely primarily on combinations of inhalation agents and muscle relaxants. This combination provides good surgical conditions and apparent safety and predictability; however, Stress Theory suggests that the persistent elevations in systemic vascular resistance and blood viscosity and coagulability associated with this technique may be caused by inadequately controlled somatic stress that may increase risk. The associated increases in blood pressure are customarily treated with increased concentrations of inhalation agent or intravenous hypnotic agents in the belief that hypnotic agents reduce sympathetic tone and activity levels. However, neither hypnotics nor muscle relaxants prevent the release of hormones in response to somatic stress, and large doses of hypnotics are known to cause direct myocardial depression. Hypnotics may thus reduce blood pressure by depressing cardiac output rather than by controlling SNS activity. Low blood pressure is accordingly viewed with alarm by anesthesiologists, who regard it primarily as a warning of dangerous cardiac depression caused by anesthetic agents. In consequence, opioids and conduction anesthesia techniques are often avoided or used with great caution due to their tendency to cause hypotension when combined with hypnotics. In addition, traditional anesthesia techniques typically employ deliberate hypocarbia, which may be inherently counterproductive, and which may cause dangerous respiratory depression in the presence of generous opioid dosage. This further discourages the use of opioids.

Stress Theory suggests that blood pressure may be an inadequate and misleading standard for anesthesia monitoring and record-keeping purposes. Hypotension in the presence of the "Traditional" technique of general anesthesia, where uncontrolled somatic stress routinely causes elevations in systemic vascular resistance, is properly regarded as a warning of cardiac depression. In contrast, moderate hypotension in the presence of modern stress control techniques that employ opioids and local anesthetics in doses adequate to control somatic stress may signal the opening of the Capillary Gate, reduction in systemic vascular resistance, improved capillary bed perfusion, and the establishment of effective and desirable stress control conditions. This effect has been demonstrated most clearly in the case of combined epidural/general anesthesia techniques, where increased tissue perfusion(348) and oxygenation(85), together with improved outcome and reductions in the incidence of symptoms of Surgical Stress(349) (89) have been demonstrated despite significant reductions in blood pressure. Similar improvements in outcome together with synergistic reductions of SNS tone and blood pressure appear to occur with combinations of inhalation agents and opioids(350-353). A similar effect may explain successful therapeutic regimens for congestive heart failure that combine fibrinolytic agents such as NTP and NTG that lower systemic vascular resistance (and blood pressure) with inotropes such as dopamine that increase cardiac output. Reductions in blood pressure may reflect benefit under such circumstances. It may be that alternative means of evaluating perfusion and oxygenation can offer a monitoring standard that is more useful and less confusing than blood pressure.

Figure 3:
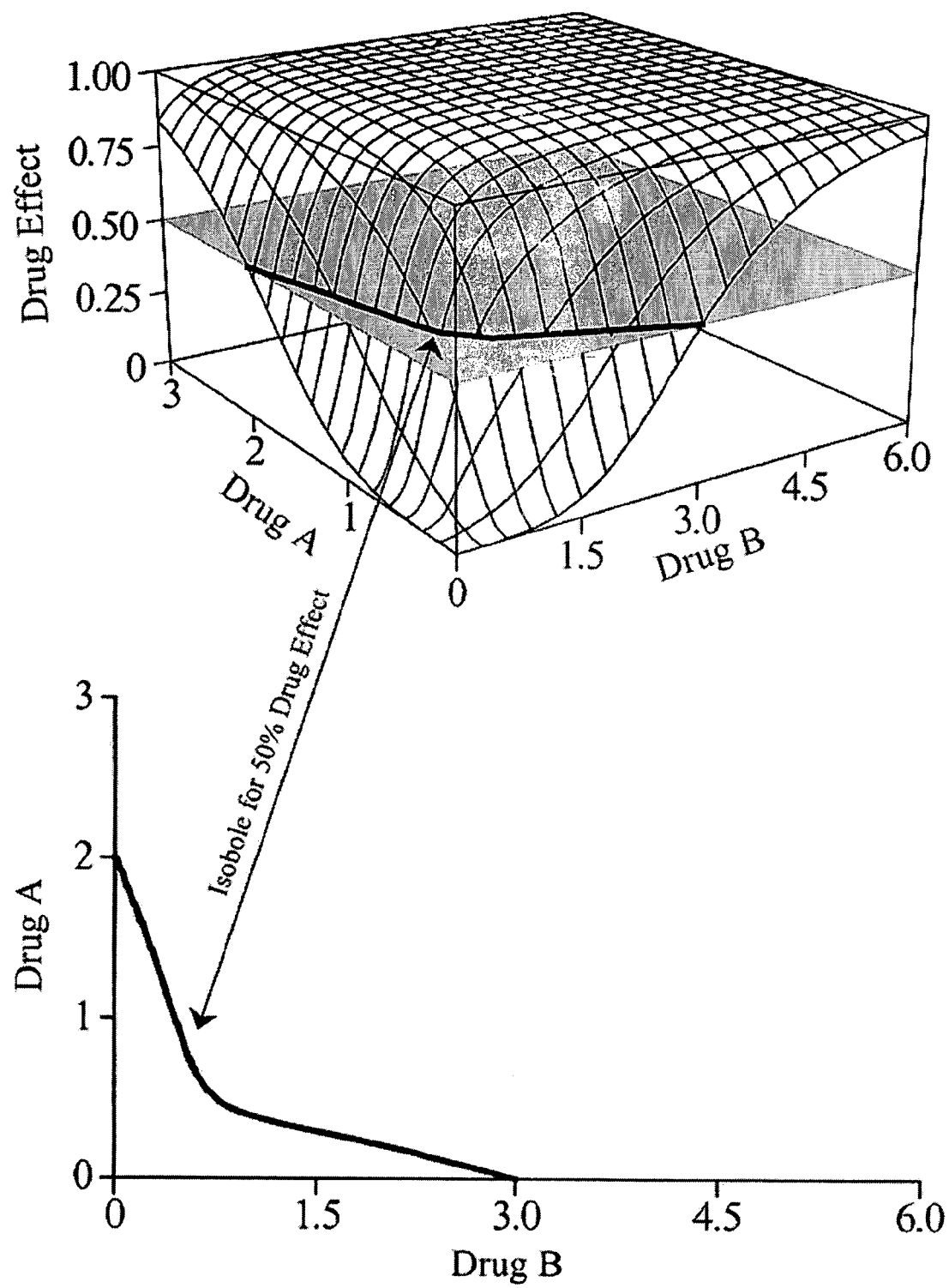
FIG. 3 shows the sigmoid concentration-response relation for three fixed ratios of drug A and drug B. The effect for any combination of drug A and drug B is described by the response surface.

Modern general anesthetic approaches consist of a two drug process involving combinations of an analgesic (opioid or local anesthetic) and a hypnotic (such as an inhalation agent) that synergize each other's effects via their respective abilities to depress SNS and CNS (Central Nervous System) activity. This can be visualized in the form of a three-dimensional "bologram" (FIG. 3). Opioids and local anesthetics produce a marked reduction in the level of hypnotic required, and vice-versa; the relationship is highly non-linear, and neither type of agent produces satisfactory results when used alone. This synergism of hypnotics and analgesics is consistent with Stress Theory, which suggests that psychic and somatic stress cause SNS activation via semi-autonomous pathways.

These scientific principles may be exploited to optimize desirable drug effects, minimize those not desired, and devise an antinociceptive general anesthetic strategy that may optimize outcome in the manner of combined epidural-general techniques. Opioids control somatic stress in a dose-related manner, but cause minimal depression of cardiac output. Inhalation agents produce optimal control of psychic stress in below-MAC concentrations that ablate awareness, but large concentrations progressively depress cardiac output. Therefore small concentrations of inhalation agents may be combined with generous doses of opioids to achieve simultaneous control of both somatic and psychic stress, thereby theoretically optimizing control of SNS activity levels and the Stress Mechanism, with minimal direct depression of cardiac output. The interaction may also be exploited to accelerate anesthetic induction and emergence, and reduce the need for muscle relaxants, which operate via a separate mechanism and do not synergize the effects of either opioids or hypnotics. The respiratory depression that may accompany this technique can be easily managed with common respiratory support techniques that allow mild hypercarbia to offset the respiratory effects of opioid and encourage cardiac output.

In FIG. 3, the left- and rightmost edges of the surface are the sigmoid concentration-response relation for drug A and drug B, respectively. The three radial lines on the surface show the sigmoid concentration-response relation for three fixed ratios of drug A and drug B. The effect for any combination of drug A and drug B is described by the response surface. The 25, 50, and 75% effect isoboles as shown.(354).

Stress Theory might inspire fresh approaches to anesthesia. Intravenous lidocaine infusion, a once-popular anesthetic technique in North America, was abandoned after the introduction of Halothane. Surviving descriptions of the technique (355) suggest that lidocaine dosage needed to achieve adequate analgesia was associated with a pronounced cutaneous flush and mild hypotension that might be explained by reduction of Factor VIII blood levels and widespread opening of the Capillary Gate. Lidocaine infusions have been shown to control thrombophlebitis(356) and to reduce MAC(357), which may be explained by their ability to inhibit somatic stress and the release of Factor VIII(358,359),. They might offer a relatively safe and effective to achieve antinociceptive anesthesia if combined with hypnotic agents and respiratory support.

Clinical Examples

This section discusses the interpretations of selected diseases and syndromes in terms of Stress Theory and illustrate how the Theory may provide simplified and improved explanations of observed phenomena.

SIRS, ARDS, & Multi-Organ Failure

SIRS (Systemic Inflammatory Response Syndrome)(360) has four identified components: vasodilation, increased microvascular permeability, increased leukocyte and platelet activation and adhesion, and hypercoagulability(361). It tends to be associated with conditions of stress, such as trauma, sepsis(139), pancreatitis, and burns(360). Multi-Organ Failure Syndrome (MOFS), also a Critical Care phenomenon associated with sepsis and trauma and frequently observed in the Intensive Care Unit, is associated with the same types of extreme stress, and exhibits similar symptoms (95,362). These may be closely related stress states caused by activation of Factors VII and VIII. SIRS might be explained by relatively greater activation of Factor VII, causing inflammatory effects to predominate, and MOFS might be explained by relatively greater activation of Factor VIII(363), causing the effects of hyper-elevations of blood fibrin levels to predominate. Alternatively, SIRS may represent the prelude to MOFS(364) or a lower-grade activation of the Stress Mechanism. Extreme activations of the Stress Mechanism and elevations of circulating insoluble fibrin might explain the increased incidence of DIC(246,365) and the fibrin deposits(366) that appear in vital organs in MOFS(366-368).

ARDS is characterized by elevations in Factor VIII, is strongly associated with DIC(369), appears to be part of Multi-Organ Failure Syndrome(370), and serves as a prototypical example of fibrin-induced organ damage that disrupts the function of kidneys, bowel, liver, and other organs in severe stress states. Massive deposits of fibrin have been documented in pulmonary capillaries in ARDS(371,372). I hypothesize that stress-related fibrin deposits in alveolar capillaries are the cause of the ARDS syndrome. Because of the large capillary reserves that exist in normal lung, the onset of ARDS tends to be occult and insidious. Pulmonary vascular resistance is normally very low, and the accumulating fibrin may cause few noticeable symptoms until fibrin deposits have accumulated beyond a critical threshold that causes increased pulmonary vascular resistance and pulmonary perfusion pressures, and right heart failure. This would explain the apparent sudden onset of clinical symptoms that commonly inspires ineffective and potentially counter-productive efforts to treat the syndrome using ventilation techniques. Surviving patients often suffer residual pulmonary fibrosis and permanent lung damage as the stress mechanism consolidates the fibrin deposits into sclerotic lesions that reduce capillary reserve. I hypothesize that a similar stress phenomenon resulting in acute thrombin-mediated deposition of fibrin in lung capillaries combined with thrombin-mediated fibroblast activation(373) may largely explain asthma(374), High Altitude Pulmonary Edema (HAPE)(375-378), cor pulmonale (379), the pulmonary manifestations of acute CHF, and other lung pathologies(15).

Shock

I hypothesize that shock states, including cardiogenic shock, septic shock, and hypovolemic shock, are caused by combinations of stress-related closure of the Capillary Gate that causes increased systemic vascular resistance and CFS (187) and low cardiac output. The SNS may regulate closure of the Capillary Gate so as to direct limited cardiac output preferentially to vital organs such as the heart and brain to preserve life, while other tissues may suffer hypoxic damage due to exaggerated CFS under such circumstances. Shock states are associated with elevations of SNS tone, systemic vascular resistance, Factor VIII, blood viscosity and coagulability, and blood levels of insoluble fibrin(380). "Second Tier" organs such as kidneys and bowel that normally require high perfusion rates may be particularly vulnerable to CFS under such circumstances, and the stress-related elevations in blood levels of insoluble fibrin may explain the renal "casts" (381,382), acute tubular necrosis, and bowel ileus that occur in such conditions. I hypothesize that the heart and brain are relatively resistant to the effects of CFS, but not immune. This might be partly explained by the activity of astrocytes in the brain(64) which may mediate the release of both fibrinolytic and fibrin-enhancing substances from the vascular endothelium that preserve brain capillary blood flow in hypotensive states(383). Astrocytes may be specialized neurons that control the release of stress-related hormones from the vascular endothelium(64) that regulate the Capillary Gate in addition to the Stress Mechanism. The activity of astrocytes may thus largely explain "cerebral autoregulation".

Eclampsia

Normal pregnancy is a stressful condition(384) that is associated with above-normal levels of Factor VIII and blood coagulability(141,242). It is associated with other stress-related conditions, such as diabetes, and may aggravate them (385). Eclampsia is a stress state that involves levels of blood coagulability and Factor VIII that are elevated above those of normal pregnancy(40,188), and the severity of eclamptic symptoms mirrors the elevations in Factor VIII and blood coagulability(386,387). A common source of additional stress that may convert a normal pregnancy into an eclamptic state is sepsis resulting from pyelonephritis(388,389). The risk of eclampsia is increased by the presence of other stress states, such as diabetes(390). In the most severe manifestation of eclampsia, known as HELLP Syndrome, there is severe risk of DIC(218,391) that may be initiated by amniotic fluid embolus(392), and visible fibrin deposits appear in various organs, causing disturbed organ function(243,244,393). Fibrin deposition on placental villi interferes with fetal growth and development, and may cause miscarriage. Fibrin deposits in the liver can disturb liver function and cause the organ to swell and burst, with fatal consequences.

I hypothesize that occult fibrin deposits in the renal arterioles disturb juxtaglomerular apparatus function, and cause activation of the renin-angiotensin-aldosterone reflex in a manner analogous to that observed in classical Goldblatt kidney. This might explain the severe water retention, cerebral and peripheral edema, and electrolyte disturbances observed in eclampsia. I hypothesize that a similar stress mechanism explains so-called "essential" hypertension and may be the major cause of renal failure(394).

Magnesium sulfate, the most effective treatment for eclampsia, has powerful anticoagulant properties(312), and reduces blood fibrin levels. It has recently been shown to be surprisingly effective in the treatment of pheochromocytoma symptoms(313), perhaps via similar properties. Magnesium deficiency is associated with arrhythmnias, hypertension, neural and psychiatric disturbances(395), and sudden ischemic death. I hypothesize that the therapeutic effects of magnesium sulfate are explained by its ability to interfere with the formation of insoluble fibrin, open the Capillary Gate, and inhibit CFS(311,396). I hypothesize that it may offer an effective treatment for other acute manifestations of stress, such as ARDS and multi-organ failure.

Diabetes

Diabetes is a stressful condition in which cellular glucose deprivation causes SNS activation and elevations in blood levels of stress hormones, including glucagon and Factor VIII. This may be opposed by parasympathetic activity(306). The effects of glucagon cause elevations of blood glucose that characterize the disease, but evidence that elevated levels of blood glucose cause tissue damage is lacking. The elevation of stress hormones appears to interfere with the transport of glucose into cells, causing additional stress and further aggravating the problem in the form of a "vicious cycle". The chronic stressful stimulus causes persistent elevations in fibrinogen(274), fibrin, viscosity, and coagulability that disturb blood rheology(236,292)and microcirculation(397). Chronic CFS may explain the inexorable tissue and organ damage that occurs over time(398). Careful management of cellular hypoglycemia using insulin and measures to alleviate stress, and direct treatments that reduce blood viscosity have been shown to improve capillary blood flow(399) and diabetic symptoms(400).

Amyloidosis may play an important role in diabetes(401-403) as a cause and/or an effect. Amyloidosis is associated with increased fibrin turnover, which is characteristic of stress states, and there is a strong correlation between diabetes and Alzheimer's Disease, which is caused by amyloid deposits. There is evidence that amyloid protein may be involved with the destruction of insulin-producing cells in the pancreas (402,404).

The known increases in morbidity and mortality associated with the treatment of diabetes using sulfonamide compounds may be explained by the fact that these drugs cause a lowering of blood glucose levels, thereby aggravating stressful cellular glucose starvation, SNS activation and glucagons release. The observed increase in morbidity and to mortality associated with these drugs may be due to their tendency to activate the Stress Mechanism.

Future Directions

Stress Theory suggests numerous avenues of research and treatment. Additional research is needed to challenge Stress Theory and clarify its mechanisms. Animal research is needed to determine the most effective anesthetic approach to maintain capillary perfusion and tissue oxygenation. The possible role of other enzymatic proteins known to be associated with the coagulation process must be evaluated with respect to the Theory. For example, Factor V Leiden(405,406), which appears to oppose the effects of thrombin and Factor VIII, might function to maintain the Capillary Gate in an "open" state except in conditions of acidosis and low calcium(407). The role of Factors IX ("Christmas Factor") and X(408) may be clarified(409).

Studies are needed to evaluate the possibility that combinations of anti-thrombin agents, Factor VII inhibitors, and stress control techniques, such as lidocaine infusions, may offer more effective treatment of malignancy, rheumatoid diseases, eclampsia, diabetes and other pathologic manifestations of stress mechanism hyperactivity. Rheopheresis therapies may relieve CFS in a wide variety of pathologies (410). Research may reveal better approaches to controlling surgical stress and CFS safely and conveniently via modification of the stress mechanism at several levels. Medications and treatments might be variously directed at the hypothalamus, Sympathetic Nervous System, Vascular Endothelium, thrombin(411), insoluble fibrin, plasminogen, or Factors VII, VIII and XIII.

New anesthesia monitoring devices might be developed that could offer ways to detect activation of the stress mechanism, and rapidly evaluate the success of stress control measures and treatments(412-415). Perhaps pulse oximeter technology could be modified to detect elevations in the blood levels of insoluble fibrin. EKG machines could be merged with ANSAR technology and non-invasive computerized cardiac output technologies to provide continuous appraisal of stress-related effects. Non-invasive is techniques to monitor tissue oxygen saturation, as a reflection of capillary perfusion, might be possible. Adapting oscillometric blood pressure technology to monitor variations in blood turbulence, as a reflection of blood levels of insoluble thrombin, may offer yet another possibility. Better clinical strategies for controlling the stress mechanism during and after surgery may be sought.

Improved understanding of blood viscosity and rheology might offer better guides to red cell and platelet transfusion. New intravenous fluid preparations might be devised that would better maintain physiologic blood viscosity, coagulability(416) and rheology and produce improved vasomotor stability compared to presently available colloids(417) and crystalloids. Cardiac bypass pump technology might be modified so as to impart physiologic levels of turbulence and mixing into the infuscate; this might mitigate "pump head syndrome" and coagulability problems associated with bypass surgery. Similar considerations might apply to the design of artificial heart and ventricular assist devices.

The problems associated with blood transfusion(239) and over-utilization of crystalloids and colloids might be reduced by the availability of such an intravenous fluid. Unexpected benefits might accrue from improved maintenance of normal levels of blood viscosity and rheology, such as reduction in the incidence of PONV, the cause of which remains poorly understood.

Stress Theory might inspire new techniques and medications to minimize spinal cord damage in the presence of acute injury, speed wound healing, reduce infection, and enable tissue repairs that are presently unimaginable. It may lead to better techniques for athletic conditioning and performance. It might also suggest practical ways to extend longevity via better prevention and treatment of atherosclerosis and amyloidosis.

These suggestions represent only a few of the possibilities offered by Stress Theory.

For example, Antinociception Anesthesia method of general anesthesia improves surgical outcome by controlling and reducing psychic and somatic surgical stress simultaneously, and is preferably employed continuously before, during and after invasive surgical procedures to prevent surgical stress syndrome. Antinociception Anesthesia may additionally be employed in the treatment of malignancies and in treating atherosclerosis. Antinociception Anesthesia is based upon preventing pathological elevations in Factor VIII blood levels that increase blood viscosity and decrease capillary bed perfusion (a.k.a. capillary fibrin stress) that cause surgical stress syndrome. Antinociception Anesthesia preferably comprises at least one step, and may comprise multiple steps, from the group consisting of: controlling psychic stress, controlling somatic stress, avoiding hypocarbia, avoiding hypoxemia, avoiding hypovolemia, avoiding hypervolemia and other forms of non-surgical stressful stimuli; inducing mild hypercarbia. and maintaining normal body temperatures at all times.

For example, psychic stress may be controlled by using Sevoflurance or equivalent anesthetic inhalation agents or intravenous hypnotic drugs. Where Sevoflurance is used, it is preferably used in about 0.5 MAC concentrations.

Somatic stress may be controlled by using Fentanyl, which is preferably administered intravenously and may be administered in a loading dose of from about 2 to about 10 micrograms/kg before surgical incision. Alternately, an equivalent dosage with other opioid medications such as sufentanil may be used. Treatment of somatic stress is may be supplemented by employing additional doses of opioid to prevent sympathetic nervous system activation and/or the respiratory rate may be maintained between about 8 to about 12 breaths/minute before emergence. Somatic stress may also be controlled using intravenous infusions of lidocaine as an alternative to, or as a supplement to, treatment with opioids. For example, an intravenous infusion of lidocaine at about 0.05 to about 1 mg/kg/hour may be used to prevent somatic stress.

Mild hypercarbia may be induced by endotracheal intubation and the use of controlled ventilation, preferably with continuous monitoring. Mild hypercarbia is preferably at about 50 torr to support respiratory drive in the presence of opioid dosage and to encourage cardiac output and tissue perfusion. Also, mask induction is preferably employed for increased safety and to eliminate the need for intravenous hypnotic agents that may prolong emergence. The above-referenced techniques to reduce activation of the Stress Syndrome may also be employed to treat malignant tumors, metastatic malignancies and systemic inflammatory states.

Malignant tumors, metastatic malignancies and systemic inflammatory conditions may be treated by techniques and medications that inhibit the Stress Mechanism via different pathways so as to synergistically reduce the production and/or function of thrombin. The reduction in thrombin may occur systemically and/or locally. Methods to reduce thrombin in the treatment of tumors, metastatic malignancies and systemic inflammatory conditions may include induction and maintenance of Antinociception Anesthesia as described herein throughout the treatment process to control psychic and somatic stress and Factor VIII levels. Additionally, medications that reduce the activity levels of Factor VII may be employed as a supplement or as an alternative.

By way of example only, Factor VII inhibitors, such as LMWH (low molecular weight heparin or tinzaparin); UFH (unfractionated heparin), TFPI (tissue factor pathway inhibitor synthesized by the vascular endothelium); anti-Factor Vlla and other blockers of Factor Vlla, Xa-TFPI complex, Reviparin, rNAPc2 (nematode/hookworm anticoagulant protein), recombinant tissue factor pathway inhibitor, AP-1 (monoclonal anti-TF antibody), PHA-798, enoxaparin, dalteparin, compound 34 (pyrazinone TF/VIIa inhibitor, available from Pfizer) and low doses of warfarin may be used alone or in combination with other coagulation inhibitors to decrease the above-noted effects of the stress syndrome.

To decrease the effects of the stress syndrome and to aid in treating conditions such as for example, atherosclerosis, malignant tumors, metastatic malignancies and systemic inflammatory states, a suitable dosage of tinzaparin may be from about 75 U/kg qd to about 175 U/kg qd; for enoxaparin a suitable dosage may be about 1 mg/kg bid, and for dalterparin, a suitable dosage may be about 120 U/Kg bid, and a suitable dosage of Raviparin may be about 10 mg/kg or about 30 to about 50 IU/kg Q about 12 hours. A suitable dosage of UFH for the treatments described herein may be determined on the basis of APTT (activated partial thromboplastin time) 2 times normal or whole-blood clotting time 3 times control value. A suitable dosage of rNAPc2 may be about 3 micrograms/kg. A suitable dosage of PHA-798 may be from about 100 to about 200 mcg/kg/minute.

Coagulation inhibitors may also be used in combination with apoptosis to treat malignancy. For example, coagulation inhibitors in combination with chemotherapy agents such as camptothecin and fas ligand may be used.

Techniques and medications that inhibit the Stress Mechanism and/or reduce the production and/or function of thrombin, including for the treatment of tumors, metastatic malignancies, atherosclerosis and systemic inflammatory conditions, may additionally include the administration of medications that reduce the activity levels of thrombin, Factor X and Factor Xa and techniques that avoid hypothermia, hypocarbia, hypoxia, hyperoxia and other stressful stimuli that may activate the stress syndrome. For example, rTAP (recombinant tick anti-coagulant protein); tinzaparin, Fondaparinux and rNAPc2, Indraparinux and Parnaparin may be used to reduce the levels of Factor X and Factor Xa. A suitable dosage of rTAP may be about 1 mg/kg bolus followed by 3 mg/kg per hour. A suitable dosage of tinzaparin may be about 175 U/kg. A suitable dosage of Fondaparinux may be from about 2.2 to about 10 QD. A suitable dosage of rNAPc2 may be from about 0.3 to about 5 microgram/kg, and a suitable dosage of Parnaparin may be about 100 IU/kg.

Suitable thrombin inhibitors may include, for example, warfarin (coumadin), annexin V, Ximelagatran, Melagatran, hirudin, bivalirudin, and argatroban. A suitable dosage of Ximelagatran may be from about 24 to about 36 mg bid orally. Melagatran may be administered intravenously or subcutaneously. A suitable dosage of warfarin may be from about INR 2.0 to about INR 3.0. As suitable dosage of Hirudin may be from about 0.006 to about 0.24 mg/kg/hour IV infusion. A suitable dosage of bivalirudin may be about 0.75 mg/kg bolus and about 1.75 mg/kg hour infusion. A suitable dosage of argatroban may be from about 0.5 to about 2 micrograms/kg/minute.

Suitable inhibitors of Factor VIII may include, for example, local anesthetic infusions, opioids, and sedative-hypnotic agents and inhalation agents, and combinations thereof.

The above-referenced compounds and medications that inhibit the Stress Mechanism and Factor VIII, Factor VII, Factor X, Factor Xa and thrombin may be delivered by employing a skin patch or skin peel. For example, the above-referenced medications may be delivered via a skin patch or skin peel to induce localized apoptosis to treat skin malignancies and other abnormal skin lesions. Suitable skin patch and skin peel technologies may include materials marketed by Zars, Inc. of Salt Lake City, Utah.

Avoiding hypothermia, hypocarbia, hypoxia, hyperoxia, and other stressful stimuli that may cause activation of the stress mechanism may also be used alone or in combination with the methods and compositions disclosed herein to reduce the stress mechanism and to treat atherosclerosis, improve surgical outcome, treat tumors, metastatic malignancies, and systemic inflammatory conditions. For example, use of tube feeding techniques to the distal ileum may be employed to prevent activation of the stress syndrome due to starvation during the treatment process. Careful padding may be used to protect the patient's body form trauma that might hemorrhage in the presence of suppression of blood coagulation. Use of special beds to regularly change the patient's body position and thereby minimize the risk of pressure injury may be used. The patient may be emerged from anesthesia after completion of treatment and restoration of safe levels of blood coagulability.

Atherosclerosis may be treated and reversed by decreasing the stress mechanism by way of medications and techniques and/or by increasing blood turbulence and mixing. For example, ultrasound may be used to increase blood turbulence and mixing. Ultrasound may be induced in the blood via external ultrasound devices and/or induced by pulsed laser radiation. The pulsed laser radiation may be delivered via an intra-arterial fiberoptic catheter. Ultrasound may also be generated externally and delivered to the intra-arterial treatment location via an intra-arterial catheter, or generated at the tip of an intra-arterial catheter by a miniaturized ultrasound generator device.

Blood viscosity may also be decreased by reducing blood levels of red cell mass, by reducing blood levels of fibrin and fibrinogen by plasmapheresis or medications, or combinations thereof.

An intravenous blood substitute solution preferably comprises fibrinogen, albumen, and electrolytes. The electrolytes may include sodium, potassium, magnesium and trace elements found in normal blood. The fibrinogen may comprise human fibrinogen, animal fibrinogen and combinations thereof. The blood substitute may be used for rapidly restoring normal blood viscosity, rheology, osmolarity, turbulence and mixing and hemodynamic stability.

While the present invention has been described with regards to particular embodiments, it is recognized that additional variations of the present invention may be devised without departing from the inventive concept.

What is claimed is:

1. A method for treating a malignant tumor in an organism in need thereof by reducing a stress mechanism and synergistically reducing production of thrombin in the organism, the method comprising:
   a. administering antinociception anesthesia to control psychic and somatic stress mechanisms and to reduce Factor VIII activity;
   b. administering a Factor VII inhibitor to reduce Factor VII activity in the organism, wherein the Factor VII inhibitor is selected from the group consisting of low molecular weight heparin, unfractionated heparin, reviparin, enoxaparin, dalteparin, tissue factor pathway inhibitor, Xa-tissue factor pathway inhibitor complex, nematode/hookworm anticoagulant protein (rNAPc2), anti-Factor VIIa compound, recombinant tissue factor pathway inhibitor, monoclonal anti-TF antibody, PHA-798 and compound 34 (pyrazinone TF/VIIa inhibitor);
   c. administering an anti-thrombin medication to the organism, wherein the anti-thrombin medication comprises a compound selected from the group consisting of hirudin, coumadin, annexin V, ximelagatran, bivalirudin, melagatran, and argatroban; and
   d. reducing a stressful condition selected from the group consisting of hypovolemia, hypervolemia, hypoxemia, hyperoxia, hypocarbia, and hypothermia, thereby treating the malignant tumor in the organism.

2. The method of claim 1, wherein coumadin is administered at a dose of about International Normalized Ratio ("INR") 2.0 to about INR 3.0.

3. The method of claim 1, wherein ximelagatran is administered at a dose of about 24 mg bis in die (bid) to about 36 mg bid orally.

4. The method of claim 1, wherein bivalirudin is administered at a dose of about 0.75 mg/kg bolus to about 1.75 mg/kg/hour infusion.

5. The method of claim 1, wherein argatroban is administered at a dose of about 0.5 microgram/kg/minute to about 2 micrograms/kg/minute.

6. The method of claim 1, wherein low molecular weight heparin is administered at a dose of about 75 U/kg quaque die to about 175 U/kg quaque die.

7. The method of claim 1, wherein enoxaparin is administered at a dose of about 1 mg/kg bis in die.

8. The method of claim 1, wherein reviparin is administered at a dose of about 10 mg/kg.

9. The method of claim 1, wherein reviparin is administered at a dose of about 30 IU/Kg quaque die about 12 hours to about 50 IU/kg quaque die about 12 hours.

10. The method of claim 1, wherein a dosage of unfractionated heparin is selected from the group consisting of a dosage sufficient to achieve two times normal activated partial thromboplastin time ("APTT") and a dosage sufficient to achieve three times the control value for whole blood clotting time.

11. The method of claim 1, wherein rNAPc2 is administered at a dose of about 3 micrograms/kg.

12. The method of claim 1, wherein PHA-798 is administered at a dose of approximately 100 mcg/kg/minute to approximately 200 mcg/kg/minute.

13. The method of claim 1, wherein dalteparin is administered at a dose of about 120 U/Kg bis in die.

14. The method of claim 1, further comprising a Factor X inhibitor and a Factor Xa inhibitor, wherein the Factor X inhibitor and the Factor Xa inhibitor are selected from the group consisting of recombinant tick anti-coagulant protein ("rTAP"), tinzaparin, fondaparinux, rNAPc2, idraparinux and parnaparin.

15. The method of claim 14, wherein parnaparin is administered at a dose of about 100 IU/kg.

16. The method of claim 14, wherein rNAPc2 is administered at a dose of about 0.3 microgram/kg to about 5 microgram/kg.

17. The method of claim 14, wherein fondaparinux is administered at a dose of about 2.2 mg quaque die to about 10 mg quaque die.

18. The method of claim 14, wherein tinzaparin is administered at a dose of about 175 IU/kg.

19. The method of claim 14, wherein rTAP is administered at a dose of about 1 mg/kg bolus followed by about 3 mg/kg per hour.

20. A method for treating a malignant tumor in an organism in need thereof by reducing a stress mechanism and synergistically reducing production of thrombin in the organism, the method comprising:
   a. administering antinociception anesthesia to control psychic and somatic stress mechanisms and to reduce Factor VIII activity;
   b. administering a Factor VII inhibitor to reduce Factor VII activity in the organism, wherein the Factor VII inhibitor is selected from the group consisting of low molecular weight heparin, unfractionated heparin, reviparin, enoxaparin, dalteparin, tissue factor pathway inhibitor, Xa-tissue factor pathway inhibitor complex, nematode/hookworm anticoagulant protein (rNAPc2), anti-Factor VIIa compound, recombinant tissue factor pathway inhibitor, monoclonal anti-TF antibody, PHA-798 and compound 34 (pyrazinone TF/VIIa inhibitor);
   c. administering an anti-thrombin medication to the organism, wherein the anti-thrombin medication comprises a compound selected from the group consisting of hirudin, coumadin, amexin V, ximelagatran, bivalirudin, melagatran, and argatroban; and
   d. inducing a mild hypercarbia to increase carbon dioxide levels in blood, thereby treating the malignant tumor in the organism.

21. A skin patch for treating a skin malignancy in an organism in need thereof, wherein said skin patch comprises an anti-thrombin medication selected from the group consisting of coumadin, melagatran, annexin V, ximelagatran, bivalirudin and argatroban.

22. The skin patch of claim 21, further comprising a Factor VII inhibitor selected from the group consisting of low molecular weight heparin, tinzaparin, reviparin, enoxaparin, daltepari, unfractionated heparin, tissue factor pathway inhibitor, Xa-tissue factor pathway inhibitor complex, nematode/hookworm anticoagulant protein (rNAPc2), anti-Factor VIIa compound, recombinant tissue factor pathway inhibitor, monoclonal anti-TF antibody, PHA-798, and compound 34 (pyrinone TF/VIIa inhibitor).

* * * * *